(12) United States Patent
Koller et al.

(10) Patent No.: US 10,978,174 B2
(45) Date of Patent: Apr. 13, 2021

(54) BARCODE SEQUENCES, AND RELATED SYSTEMS AND METHODS

(71) Applicant: LIFE TECHNOLOGIES CORPORATION, Carlsbad, CA (US)

(72) Inventors: Christian Koller, San Francisco, CA (US); Michael D. Allen, Encinitas, CA (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 1004 days.

(21) Appl. No.: 15/154,499

(22) Filed: May 13, 2016

(65) Prior Publication Data

US 2016/0333402 A1    Nov. 17, 2016

Related U.S. Application Data

(60) Provisional application No. 62/161,309, filed on May 14, 2015.

(51) Int. Cl.
*G16B 30/00*       (2019.01)
*C12Q 1/6869*      (2018.01)
*C12Q 1/6874*      (2018.01)

(52) U.S. Cl.
CPC .......... *G16B 30/00* (2019.02); *C12Q 1/6869* (2013.01); *C12Q 1/6874* (2013.01)

(58) Field of Classification Search
None
See application file for complete search history.

(56) References Cited

U.S. PATENT DOCUMENTS 2,632,058 A    3/1953  Gray
4,683,195 A    7/1987  Mullis et al.
(Continued)

FOREIGN PATENT DOCUMENTS

CN    101457253 A    6/2009
EP    2053132 A1     4/2009
(Continued)

OTHER PUBLICATIONS

1. Bystrykh, L. V. Generalized DNA barcode design based on Hamming codes. PLoS ONE 7, e36852:1-8 (2012).*
(Continued)

*Primary Examiner* — Soren Harward
(74) *Attorney, Agent, or Firm* — Jones Robb, PLLC

(57) ABSTRACT

Methods, system, and kits are provided for sample identification, and, more specifically, for designing, and/or making, and/or using sample discriminating codes or barcodes for identifying sample nucleic acids or other biomolecules or polymers. For example, a plurality of flowspace codewords may be generated, the codewords comprising a string of characters. A location for at least one padding character within the flowspace codewords may be determined. The padding character may be inserted into the flowspace codewords at the determined location. After the inserting, a plurality of the flowspace codewords may be selected based on satisfying a predetermined minimum distance criteria, wherein the selected codewords correspond to valid base space sequences according to a predetermined flow order. And the barcode sequences corresponding to the selected codewords may be manufactured.

16 Claims, 11 Drawing Sheets

Specification includes a Sequence Listing.

(56) References Cited

U.S. PATENT DOCUMENTS

| | | |
|---|---|---|
| 4,683,202 A | 7/1987 | Mullis |
| 4,800,159 A | 1/1989 | Mullis et al. |
| 4,965,188 A | 10/1990 | Mullis et al. |
| 5,210,015 A | 5/1993 | Gelfand et al. |
| 5,399,491 A | 3/1995 | Kacian et al. |
| 5,750,341 A | 5/1998 | Macevicz |
| 5,854,033 A | 12/1998 | Lizardi |
| 6,172,214 B1 | 1/2001 | Brenner |
| 6,174,670 B1 | 1/2001 | Wittwer et al. |
| 6,210,891 B1 | 4/2001 | Nyren et al. |
| 6,235,475 B1 | 5/2001 | Brenner et al. |
| 6,251,639 B1 | 6/2001 | Kurn |
| 6,258,568 B1 | 7/2001 | Nyren |
| 6,274,320 B1 | 8/2001 | Rothberg et al. |
| 6,404,907 B1 | 6/2002 | Gilchrist et al. |
| 6,780,591 B2 | 8/2004 | Williams et al. |
| 6,828,100 B1 | 12/2004 | Ronaghi |
| 6,833,246 B2 | 12/2004 | Balasubramanian |
| 6,911,327 B2 | 6/2005 | McMillan et al. |
| 7,037,687 B2 | 5/2006 | Williams et al. |
| 7,049,645 B2 | 5/2006 | Sawada et al. |
| 7,117,095 B2 | 10/2006 | Hubbell |
| 7,133,782 B2 | 11/2006 | Odedra |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,323,309 B2 | 1/2008 | Mirkin et al. |
| 7,335,762 B2 | 2/2008 | Rothberg et al. |
| 7,348,181 B2 | 3/2008 | Walt et al. |
| 7,424,371 B2 | 9/2008 | Kamentsky |
| 7,535,232 B2 | 5/2009 | Barbaro et al. |
| 7,575,865 B2 | 8/2009 | Leamon et al. |
| 7,645,596 B2 | 1/2010 | Williams et al. |
| 7,695,907 B2 | 4/2010 | Miyahara et al. |
| 7,782,237 B2 | 8/2010 | Ronaghi et al. |
| 7,785,862 B2 | 8/2010 | Kim et al. |
| 7,835,871 B2 | 11/2010 | Kain et al. |
| 7,838,226 B2 | 11/2010 | Kamahori et al. |
| 7,867,703 B2 | 1/2011 | Sampson et al. |
| 7,875,440 B2 | 1/2011 | Williams et al. |
| 7,888,013 B2 | 2/2011 | Miyahara et al. |
| 7,948,015 B2 | 5/2011 | Rothberg et al. |
| 8,058,055 B2 | 11/2011 | Barrett et al. |
| 8,202,691 B2 | 6/2012 | Steemers et al. |
| 8,262,900 B2 | 9/2012 | Rothberg et al. |
| 8,306,757 B2 | 11/2012 | Rothberg et al. |
| 8,309,307 B2 | 11/2012 | Barrett et al. |
| 8,568,979 B2 | 10/2013 | Stuelpnagel et al. |
| 8,673,627 B2 | 3/2014 | Nobile et al. |
| 2003/0219797 A1 | 11/2003 | Zhao et al. |
| 2003/0232348 A1 | 12/2003 | Jones et al. |
| 2004/0018506 A1 | 1/2004 | Koehler et al. |
| 2004/0197793 A1 | 10/2004 | Hassibi et al. |
| 2004/0197845 A1 | 10/2004 | Hassibi et al. |
| 2005/0084851 A1 | 4/2005 | Ronaghi et al. |
| 2006/0147935 A1 | 7/2006 | Linnarsson |
| 2006/0147983 A1 | 7/2006 | O'uchi et al. |
| 2007/0059733 A1 | 3/2007 | Sundararajan et al. |
| 2007/0059741 A1 | 3/2007 | Kamahori et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0166727 A1 | 7/2008 | Esfandyarpour et al. |
| 2008/0182757 A1 | 7/2008 | Heiner et al. |
| 2008/0274904 A1 | 11/2008 | Gormley et al. |
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2009/0221438 A1 | 9/2009 | Kitzman et al. |
| 2009/0312188 A1 | 12/2009 | Duer et al. |
| 2010/0029498 A1 | 2/2010 | Gnirke et al. |
| 2010/0035252 A1 | 2/2010 | Rothberg et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0065604 A1 | 3/2011 | Sampson et al. |
| 2011/0160078 A1 | 6/2011 | Fodor et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0046175 A1 | 2/2012 | Rodesch et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2012/0220494 A1 | 8/2012 | Samuels et al. |
| 2012/0264621 A1 | 10/2012 | Hubbell et al. |
| 2012/0301926 A1 | 11/2012 | Chen et al. |
| 2013/0053256 A1 | 2/2013 | Hubbell |
| 2013/0060482 A1 | 3/2013 | Sikora et al. |
| 2014/0233232 A1 | 8/2014 | Meredith et al. |
| 2015/0087537 A1 | 3/2015 | Hubbell |
| 2017/0321271 A1 | 11/2017 | Hubbell |

FOREIGN PATENT DOCUMENTS

| | | |
|---|---|---|
| GB | 2461127 | 12/2009 |
| WO | WO-2001/001015 | 1/2001 |
| WO | WO-2005/040425 | 5/2005 |
| WO | 2006084131 A2 | 8/2006 |
| WO | WO-2008/076406 | 6/2008 |
| WO | WO-2009/158006 | 12/2009 |
| WO | 2010003153 A2 | 1/2010 |
| WO | WO-2010/047804 | 4/2010 |
| WO | 2010051978 A1 | 5/2010 |
| WO | WO-2010/077859 | 7/2010 |
| WO | 2010122506 A2 | 10/2010 |
| WO | WO-2010/117804 | 10/2010 |
| WO | WO-2010/138182 | 12/2010 |
| WO | WO-2012/044847 | 4/2012 |
| WO | 2012129363 | 9/2012 |
| WO | 2013010062 A2 | 1/2013 |

OTHER PUBLICATIONS

Lennon, N. J. et al. A scalable, fully automated process for construction of sequence-ready barcoded libraries for 454. Genome Biology 11, (2010).*

Parameswaran, P. et al. A pyrosequencing-tailored nucleotide barcode design unveils opportunities for large-scale sample multiplexing. Nucleic Acids Research 35, e130:1-9 (2007).*

(56) References Cited

OTHER PUBLICATIONS

Ahmadian et al., "Pyrosequencing: history, biochemistry and future," *Clin. Chim. Acta*, 363:83-94 (2006).
Aksyonov et al., "Multiplexed DNA sequencing-by-synthesis," *Anal. Biochem.*, 348:127-138 (2006).
Anderson et al., "A System for Multiplexed Direct Electrical Detection of DNA Synthesis," *Sens. Actuators B Chem.*, 129(1):79-86 (2008).
Ashlock et al., "DNA error correcting codes: No crossover," *IEEE Symposium on Computational Intelligence in Bioinformatics and Computational Biology*, 38-45 (2009).
Brockman et al., "Quality scores and SNP detection in sequencing-by-synthesis systems," *Genome Res.*, 18:763-770 (2008).
Berger et al., "Compact, universal DNA microarrays to comprehensively determine transcription-factor binding site specificities," *Nat. Biotechnol.*, 24(11):1429-1435 (2006).
Dawson et al., "Synthesis of proteins by native chemical ligation," *Science*, 266:776-779 (1994).
Droege et al., "The Genome Sequencer FLX™ System—Longer reads, more applications, straight forward bioinformatics and more complete data sets," *J. Biotechnol.*, 136:3-10 (2008).
Eltoukhy et al., "Modeling and Base-Calling for DNA Sequencing-By-Synthesis," *2006 IEEE International Conference on Acoustics, Speech, and Signal Processing*, II:1032-1035 (2006).
Faircloth et al., "Large sets of edit-metric sequence identification tags to facilitate large-scale multiplexing of reads from massively parallel sequencing," *Nature Precedings*, 1-15 (2011).
Fakhrai-Rad et al., "Pyrosequencing™: An Accurate Detection Platform for Single Nucleotide Polymorphisms," *Hum. Mutat.*, 19:479-485 (2002).
Fu et al., "Counting individual DNA molecules by the stochastic attachment of diverse labels," *Proc. Natl. Adac. Sci. U.S.A.*, 108(22):9026-9031 (2011).
Golay, M., "Notes on Digital Coding," *Proc. IRE*, 37(6):657 (1949).
Gharizadeh, B., "Method Development and Applications of Pyrosequencing Technology," Doctoral Dissertation, Royal Institute of Technology, Stockholm, Sweden (2003).
Hamady et al., "Error-correcting barcoded primers for pyrosequencing hundreds of samples in multiplex," *Nat. Methods*, 5(3):235-237 (2008).
Hamming, R.W., "Error Detecting and Error Correcting Codes," *Bell Syst. Tech. J.*, 29(2):147-160. (1950) (available at http://www.alcatel-lucent.com/bstj/vol29-1950/articles/bstj29-2-147.pdf).
Ji et al., "BM-BC: A Bayesian method of base calling for Solexa sequence data," *Department of Biostatistics, The University of Texas M. D. Anderson Cancer Center, Houston, Texas*, U.S.A. (http://odin.mdacc.tmc.edu/~ylji/BMBC/bmbc-ie2.pdf), pp. 1-27 (2010).
Kanemasu, M., "Golay Codes," *MIT Undergraduate Journal of Mathematics*, 1:95-99 (1999) (available at http://www-math.mit.edu/phase2/UJM/vol1/MKANEM~1.PDF).
Krishnan et al., "Barcodes for DNA sequencing with guaranteed error correction capability," *Electron. Lett.*, 47(4):1-2 (2011).
Margulies et al., Supplementary Methods for the article "Genome sequencing in microfabricated high-density picolitre reactors," *Nature*, 437:376-380 (2005), pp. 1-34.
Margulies et al., "Genome sequencing in microfabricated high-density picolitre reactors," *Nature*, 437:376-380 (2005).
Muir, T., "Semisynthesis of proteins by expressed protein ligation," *Ann. Rev. Biochem.*, 72:249-289 (2003).
Muralidharan et al., "Protein ligation: an enabling technology for the biophysical analysis of proteins," *Nat. Methods*, 3:429-438 (2006).
Paulus, H., "Protein splicing and related forms of protein autoprocessing", *Annu Rev Biochem*, 69:447-496 (2000).
Pourmand et al., "Direct electrical detection of DNA synthesis," *Proc. Natl. Adac. Sci. U.S.A.*, 103(17):6466-6470 (2006).
Pourmand et al., "Multiplex Pyrosequencing," *Nucleic Acids Res.*, 30(7)(e31):1-5 (2002).
Qiu et al., "DNA Sequence-Based "Bar Codes" for Tracking the Origins of Expressed Sequence Tags from a Maize cDNA Library Constructed Using Multiple mRNA Sources," *Plant Physiol.*, 133:475-481 (2003).
Ronaghi, "Pyrosequencing Sheds Light on DNA Sequencing," *Genome Res.*, 11:3-11 (2001).
Ronaghi et al., "A Sequencing Method Based on Real-Time Pyrophosphate," *Science*, 281(5375):363-365 (1998).
Shiroguchi et al., "Digital RNA sequencing minimizes sequence-dependent bias and amplification noise with optimized single-molecule barcodes," *Proc. Natl. Adac. Sci. U.S.A.*, 109(4):1347-1352 (2012).
Yan et al., "Yeast Barcoders: a chemogenomic application of a universal donor-strain collection carrying bar-code identifiers," *Nat. Methods*, 5(8):719-725 (2008).
Page Pacific Biosciences et al: "PacBio SampleNet—Shared Protocol Guidelines for Using PacBio Barcodes for SMRT", Jan. 1, 2014.
Tilo Buschmann et al., "Levenshtein error-correcting barcodes for multiplexed DNA sequencing", BMC Bioinformatics, vol. 14, No. 1, Jan. 1, 2013.
Leonid V. Bystrykh et al., "Generalized DNA Barcode Design Based on Hamming Codes", vol. 7, No. 5, May 17, 2012.
Final Office Action in U.S. Appl. No. 14/505,636, dated Sep. 28, 2015, 16 pages.
International Search Report and Written Opinion for International Application No. PCT/US2012/046624, dated Jan. 4, 2013, 15 pages.
Mamanova, et al., "Target-enrichment strategies for next-generation sequencing", Nature Methods, vol. 7 No. 2, Feb. 2010, 111-118.
Gnirke, et al., "Solution hybrid selection with ultra-long oligonucleotides for massively parallel targeted sequencing", Nature Biotechnology, vol. 27 No. 2, Feb. 2009, 182-189.
Hodges, et al., "Hybrid selection of discrete genomic intervals on custom-designed microarrays for massively parallel sequencing", Nature Protocols, vol. 4 No. 6, 2009, 960-974.
Lee, et al., "Improving the efficiency of genomic loci capture using oligonucleotide arrays for high throughput resequencing", BMC Genomics 2009, 10:646, 12 pages.
Sakata, et al., "DNA Sequencing Based on Intrinsic Molecular Charges", Angewandte Chemie 2006, 118, 2283-2286.
Sashiardes, et al., "Direct genomic selection", Nature Methods, vol. 2 No. 1, Jan. 2005, 63-69.
Purushothaman, et al., "Towards Fast Solid State DNA Sequencing", IEEE ISCAS 2002 Proceedings, IV-169-IV-172.
Forney, et al., "The Nordstrom-Robinson Code is the Binary Image of the Octacode", Feb. 8, 2001, 11 pages.
Sakurai, et al., "Real-Time Monitoring of DNA Polymerase Reactions by a Micro ISFET pH Sensor", Anal. Chem. 1992, 64, 1996-1997.
Lin, et al., "Error Control Coding: Fundamentals and Applications", Prentice Hall, Inc., 1983.
Brenner et al., "Encoded combinatorial chemistry," Proc. Natl. Acad. Sci. USA, 89:5381-5383 (1992).
Lee, "Some Properties of Nonbinary Error-Correcting Codes," IRE Transactions on Information Theory, 77-82 (1958).
Schwartz et al., "The Structure of Single-Track Gray Codes," IEEE Transactions on Information Theory, 45(7):2383-2396 (1999).
International Search Report and Written Opinion for International Application No. PCT/US2016/032442, dated Aug. 5, 2016, 15 pages.
P. Bergveld: "Thirty years of ISFETOLOGY: what happened in the past 30 years and what may happen in the next 30 years", Sens. Actuators, vol. 88, 2003, pp. 1-20.
Wetmur, J. Mol. Biol., vol. 31, 1968, pp. 349-370.
Breslauer et al., Proceedings National Academy of Science USA, vol. 83, No. 11, 1986, pp. 3746-3750.
Casey; Davidson, Nucleic Acids Research, vol. 4, No. 5, 1977, pp. 1539-1552.
Database Geneseq, "HIV1_8 DNA amplicon flanking adaptor, SEQ ID 371", Database accession No. AYL45091 (Dec. 23, 2010).
Hawkins, Nucleic Acids Research, vol. 23, No. 15, 1995, pp. 2872-2880.
Hytonen et al., BMC Structural Biology, vol. 7, 2007, pp. 1-20.

(56) References Cited

OTHER PUBLICATIONS

Rychlik et al., Nucleic Acids Research, vol. 18, No. 21, 1990, pp. 6409-6412.
Tewhey et al., "Enrichment of sequencing targets from the human genome by solution hybridization," Genome Biology 2009, 10:R116.
Wetmur, Critical Reviews in Biochemistry and Molecular Biology, vol. 26, 1991, pp. 227-259.
EP Communication issued in corresponding European Application No. 16 726 709.5, dated Feb. 19, 2020.
Lehninger, "Biochemistry," Chapter 24: Digestion, Transport, and Integration of Metabolism, pp. 701, 702, and, 707, Worth Publishers (1982).
"PCR Primer: A Laboratory Manual," 2nd, ed., Contents, pp. vii-ix, Cold Spring Harbor Laboratory Press (2003).
Hoffman, et al., "Coding Theory: The Essentials", Pure and Applied Mathematics, Dec. 1991, including: List of 150 Monographs and Textbooks in Pure and Applied Mathematics; Preface; and pp. iii-xi: Contents, List of Figures, and List of Tables.
Baicheva, "Binary and ternary linear codes which are good and proper for error correction, in: Proceedings of the 7th International Workshop on Algebraic and Combinatorial Coding Theory," Jun. 18-24, Bansko, Bulgaria, 2000, pp. 55-60 (numbered as 6 pages).
EP Communication issued in European Application No. 16 726 709.5, dated Nov. 2, 2020.
CN Office Action issued in Chinese Application No. 201680027931.8, dated Nov. 17, 2020 (English translation provided).
Kracht, et al., "Insertion and deletion correcting DNA barcodes based on watermarks", "BMC Bioinformatics" vol. 16, Feb. 18, 2015, pp. 1-14.

\* cited by examiner

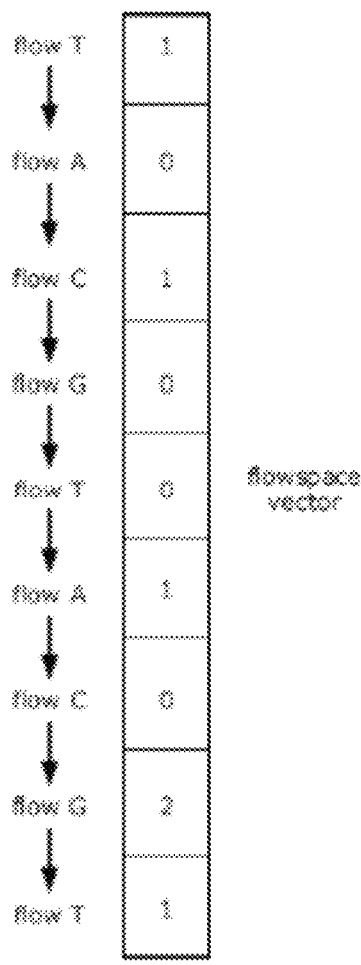
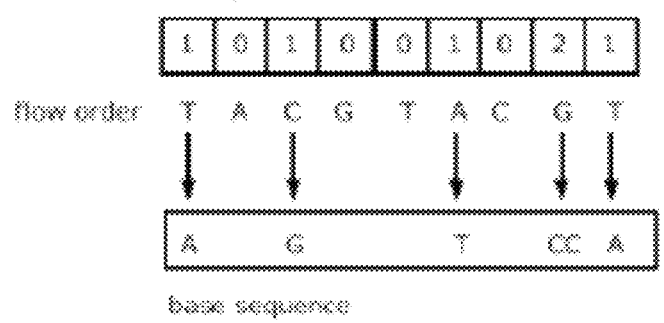
FIG. 6B
FIG. 6A

| primer site | key | barcode 1 | target sequence 1 |
| primer site | key | barcode 2 | target sequence 2 |
| primer site | key | barcode 3 | target sequence 3 |
| primer site | key | barcode 4 | target sequence 4 |
| primer site | key | barcode 5 | target sequence 5 |
| primer site | key | barcode 6 | target sequence 6 |
| primer site | key | barcode 7 | target sequence 7 |

FIG. 9

SEQUENCE LISTING

<160> NUMBER OF SEQ ID NOS: 79

<210> SEQ ID NO 1
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1
tcagtcctcg aatc             14

<210> SEQ ID NO 2
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

```
<400> SEQUENCE: 2
tcagcttgcg gatc                                                   14

<210> SEQ ID NO 3
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<400> SEQUENCE: 3
tcagtctaac ggac                                                   14

<210> SEQ ID NO 4
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
tcagttctta gcgc                                                   14

<210> SEQ ID NO 5
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
tcagtgagcg gaac                                                   14

<210> SEQ ID NO 6
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
tcagttaagc ggtc                                                   14

<210> SEQ ID NO 7
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
tcagctgacc gaac                                                   14

<210> SEQ ID NO 8
<211> LENGTH: 14
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 8
tcagtctaga ggtc                                                        14

<210> SEQ ID NO 9
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
tcagaagagg attc                                                        14

<210> SEQ ID NO 10
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tcctcgaatc                                                             10

<210> SEQ ID NO 11
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
cttgcggatc                                                             10

<210> SEQ ID NO 12
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
tctaacggac                                                             10

<210> SEQ ID NO 13
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ttcttagcgc                                                             10
```

```
<210> SEQ ID NO 14
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
tgagcggaac                                                                10

<210> SEQ ID NO 15
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ttaagcggtc                                                                10

<210> SEQ ID NO 16
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ctgaccgaac                                                                10

<210> SEQ ID NO 17
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
tctagaggtc                                                                10

<210> SEQ ID NO 18
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
aagaggattc                                                                10

<210> SEQ ID NO 19
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 19
tctgagcatc gatc                                                        14

<210> SEQ ID NO 20
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ttccggagga tgcc                                                        14

<210> SEQ ID NO 21
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ttgaggccaa gtcc                                                        14

<210> SEQ ID NO 22
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
gaccaccggt tc                                                          12

<210> SEQ ID NO 23
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
gtggacctcc gttc                                                        14

<210> SEQ ID NO 24
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
tggaccacga attc                                                        14

<210> SEQ ID NO 25
<211> LENGTH: 14
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 25
ttctggacat ccgc                                                   14

<210> SEQ ID NO 26
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
ttaggcctcc attc                                                   14

<210> SEQ ID NO 27
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
gttgaggaac cacc                                                   14

<210> SEQ ID NO 28
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ccggacaaga attc                                                   14

<210> SEQ ID NO 29
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
cggagttccg gttc                                                   14

<210> SEQ ID NO 30
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
gtccaccaac cacc                                                   14
```

```
<210> SEQ ID NO 31
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
gttccagcca tctc                                                      14

<210> SEQ ID NO 32
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gttagcggat tc                                                        12

<210> SEQ ID NO 33
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gccacaactt cc                                                        12

<210> SEQ ID NO 34
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gttccttaga agac                                                      14

<210> SEQ ID NO 35
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
gccagcacca attc                                                      14

<210> SEQ ID NO 36
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 36
gcttggagcc gttc                                                      14

<210> SEQ ID NO 37
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
tccaggcacc ttcc                                                      14

<210> SEQ ID NO 38
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
gttcctacgt tc                                                        12

<210> SEQ ID NO 39
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
ccagaacgga atcc                                                      14

<210> SEQ ID NO 40
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gtcaggacca ac                                                        12

<210> SEQ ID NO 41
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
cttaccatcc ttcc                                                      14

<210> SEQ ID NO 42
<211> LENGTH: 12
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 42
gctgacacca cc                                                              12

<210> SEQ ID NO 43
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
tcaccaacgg ac                                                              12

<210> SEQ ID NO 44
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
ctgagaatcc aacc                                                            14

<210> SEQ ID NO 45
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
ttcctacaat ctcc                                                            14

<210> SEQ ID NO 46
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
gtcttgacaa gaac                                                            14

<210> SEQ ID NO 47
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
gttcttagag aacc                                                            14
```

```
<210> SEQ ID NO 48
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
gtccaggagg tc                                                              12

<210> SEQ ID NO 49
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
tcggaccaat tgcc                                                            14

<210> SEQ ID NO 50
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
ccttaccaat aacc                                                            14

<210> SEQ ID NO 51
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
tcgaggccat cgac                                                            14

<210> SEQ ID NO 52
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ttccttacct tatc                                                            14

<210> SEQ ID NO 53
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 53
ttctgagccg ac                                                     12

<210> SEQ ID NO 54
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
gtcctaccaa tgac                                                   14

<210> SEQ ID NO 55
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
tagccaattg aacc                                                   14

<210> SEQ ID NO 56
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
gccttagcaa cacc                                                   14

<210> SEQ ID NO 57
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
gtcctgagca gaac                                                   14

<210> SEQ ID NO 58
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
gtctacctcg gc                                                     12

<210> SEQ ID NO 59
<211> LENGTH: 14
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 59
gtctgaccgg atcc                                                         14

<210> SEQ ID NO 60
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ccagaattcg gacc                                                         14

<210> SEQ ID NO 61
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
ttccggagtt catc                                                         14

<210> SEQ ID NO 62
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ccttagatcc ttcc                                                         14

<210> SEQ ID NO 63
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
gccttaggat cgcc                                                         14

<210> SEQ ID NO 64
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gccaggattg gtcc                                                         14
```

```
<210> SEQ ID NO 65
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
gtccggagat gaac                                                       14

<210> SEQ ID NO 66
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
gccttattcc aacc                                                       14

<210> SEQ ID NO 67
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
gttctaggat tcac                                                       14

<210> SEQ ID NO 68
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
tcctagtccg gtcc                                                       14

<210> SEQ ID NO 69
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gtcttggagt taac                                                       14

<210> SEQ ID NO 70
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 70
gttctatcgt tc					12

<210> SEQ ID NO 71
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ttcgagtgtt cc					12

<210> SEQ ID NO 72
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
tcttgattgg tc					12

<210> SEQ ID NO 73
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
gcttactccg gtcc					14

<210> SEQ ID NO 74
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
gattcggatt cc					12

<210> SEQ ID NO 75
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
gttcctgagt tctc					14

<210> SEQ ID NO 76
<211> LENGTH: 14
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"

<400> SEQUENCE: 76
gtcggaccat gaac                                                           14

<210> SEQ ID NO 77
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
cagatccgtt cc                                                             12

<210> SEQ ID NO 78
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
gttctgacgt cc                                                             12

<210> SEQ ID NO 79
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
tccgaggatg aatc                                                           14
```

BARCODE SEQUENCES, AND RELATED SYSTEMS AND METHODS

PRIORITY

This application claims the benefit of U.S. Prov. Pat. Appl. No. 62/161,309, filed May 14, 2015 which is incorporated by reference herein in its entirety.

SEQUENCE LISTING

The instant application contains a Sequence Listing which has been submitted electronically in ASCII format and is hereby incorporated by reference in its entirety. Said ASCII copy, created on May 12, 2016, is named LT01064_SL.txt and is 18,815 bytes in size.

FIELD

The present disclosure generally relates to methods, systems, and kits for sample identification, and, more specifically, to methods, systems, and kits for designing, and/or making, and/or using sample discriminating codes or barcodes for identifying sample nucleic acids or other biomolecules or polymers.

TECHNICAL AREA

Various instruments, apparatuses, and/or systems perform sequencing of nucleic acid sequences using sequencing-by-synthesis, including, for example, the Genome Analyzer/HiSeq/MiSeq platforms (Illumina, Inc.; see, e.g., U.S. Pat. Nos. 6,833,246 and 5,750,341); the GS FLX, GS FLX Titanium, and GS Junior platforms (Roche/454 Life Sciences; see, e.g., Ronaghi et al., SCIENCE, 281:363-365 (1998), and Margulies et al., NATURE, 437:376-380 (2005)); and the Ion PGM™ and Ion Proton™ Sequencers (Life Technologies Corp./Ion Torrent; see, e.g., U.S. Pat. No. 7,948,015 and U.S. Pat. Appl. Publ. Nos. 2010/0137143, 2009/0026082, and 2010/0282617, which are all incorporated by reference herein in their entirety). In order to increase sequencing throughput and/or lower costs for sequencing-by-synthesis (and other sequencing methods such as, e.g., sequencing-by-hybridization, sequencing-by-ligation, etc.), there is a need for new methods, systems, computer readable media, and kits that allow highly efficient preparation and/or identification of samples of potentially high complexity.

SUMMARY

The present disclosure generally relates to methods, systems, and kits for sample identification, and, more specifically, to methods, systems, and kits for designing, and/or making, and/or using sample discriminating codes or barcodes for identifying sample nucleic acids or other biomolecules or polymers. In an embodiment, a method for designing barcode sequences corresponding to flowspace codewords is provided. A plurality of flowspace codewords may be generated, the codewords comprising a string of characters. A location for at least one padding character within the flowspace codewords may be determined. The padding character may be inserted into the flowspace codewords at the determined location. After the inserting, a plurality of the flowspace codewords may be selected based on satisfying a predetermined minimum distance criteria, wherein the selected codewords correspond to valid base space sequences according to a predetermined flow order. And the barcode sequences corresponding to the selected codewords may be manufactured.

In some embodiments, after inserting the padding character, at least one codeword may be filtered that comprises an invalid base space translations according to the predetermined flow order. In some embodiments, the selected codewords collectively comprise an error tolerant code that meets the predetermined minimum distance criteria.

In some embodiments, determining a location for the padding character within the flowspace codewords may further comprise iterating over a plurality of locations for the padding character within the codewords. In addition, for each iteration, a number of codewords that correspond to a valid base space sequence according to the predetermined flow order may be calculated. The location of the plurality of locations with the highest calculated number of codewords that correspond to a valid base space sequence may then be selected.

In some embodiments, determining a location for the padding character within the flowspace codewords may further comprise determining, for each iteration, bases space sequences corresponding to the flowspace codewords that correspond to valid base space sequences after inserting the padding character at the iterated location into the codewords. For each iteration, the determined base space sequences may be filtered based on at least a length criteria for the determined sequences. And a number of valid base space sequences for the iterated location after the filtering may be calculated. In some embodiments, the filtering, for each iteration, further comprises filtering the determined base space sequences based on a percentage of nucleotide content criteria In some embodiments, the codewords of the error tolerant code are synchronized in flowspace after insertion of the at least one padding character.

In some embodiments, the generated flowspace codewords comprise a preliminary distance between the codewords such that the minimum distance between the selected codewords is greater than the minimum distance between the generated codewords. The preliminary distance between the codewords may be maintained after insertion of the padding character.

In some embodiments, selecting the plurality of codewords further comprises grouping the codewords such that an inner-group minimum distance between codewords within a group comprises a first value and an outer-group minimum distance for codewords between different groups comprises a second value, the first value being greater than the second value.

In some embodiments, a subset of the selected codewords that comprises a terminating flow that does not indicate incorporation may be determined. The subset of barcode sequences corresponding to the subset of selected codewords may be manufactured such that an adaptor for the subset of barcode sequences is selected based on the terminating flow corresponding to the subset of codewords that does not indicate incorporation.

In some embodiments, manufacturing the barcode sequences further comprises appending to the barcode sequences a series of key bases, wherein, for a first portion of the barcode sequences, the appended key bases terminate with a repeated base. For example, the first portion may comprise half of the barcode sequences. In some embodiments, for a second portion of the barcode sequences, the appended key bases may terminate with a non-repeating base. In some embodiments, the selected codewords collectively comprise an error tolerant code that comprises a minimum distance between codewords such that a variance in terminating key bases appended to the manufactured barcodes codes corresponding to the selected codewords increases the minimum distance between codewords.

In an embodiment, a method for sequencing polynucleotide samples comprising barcode sequences is provided. At least some of a plurality of barcodes may be incorporated into a plurality of target nucleic acids to create polynucleotides, wherein the plurality of barcodes are designed such that the barcodes correspond with a flowspace codeword according to a predetermined flow order, the flowspace codewords comprise one or more error-tolerant codes, and the plurality of barcodes include at least 1000 barcodes. According to the predetermined flow ordering, a series of nucleotides may be introduced to the polynucleotides. A series of signals resulting from the introducing of nucleotides to the target nucleic acids may be obtained. The series of signals may be resolved over the barcode sequences to render flowspace strings such that the rendered flowspace strings are matched to the codewords, wherein at least one rendered flowspace string is matched to at least one codeword in the presence of one or more errors. In some embodiments, the at least one rendered flowspace string that is matched to at least one flowspace codeword in the presence of one or more errors is used to identify signals obtained over one of the target nucleic acid sequences associated with the barcode corresponding to the matched flowspace codeword.

In some embodiments, a kit for use with a nucleic acid sequencing instrument is provided. The kit may comprise a plurality of barcodes sequences meeting the following criteria: the barcode sequences correspond to flowspace codewords according to a predetermined flow order such that the corresponding codewords comprise an error-tolerant code of a minimum distance of at least three; the barcode sequences have a length within a predetermined length range; the barcode sequences are synchronized in flow space; and the plurality of barcode sequences is at least 500 different barcode sequences. In some embodiments, the plurality of barcode sequences are at least 1000 different barcode sequences.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIGS. 6A and 6B demonstrate a relationship between a base space sequence and a flowspace vector.

FIG. 9 illustrates a pool of different polynucleotide strands, each with a unique barcode sequence.

DETAILED DESCRIPTION

Figure 1:
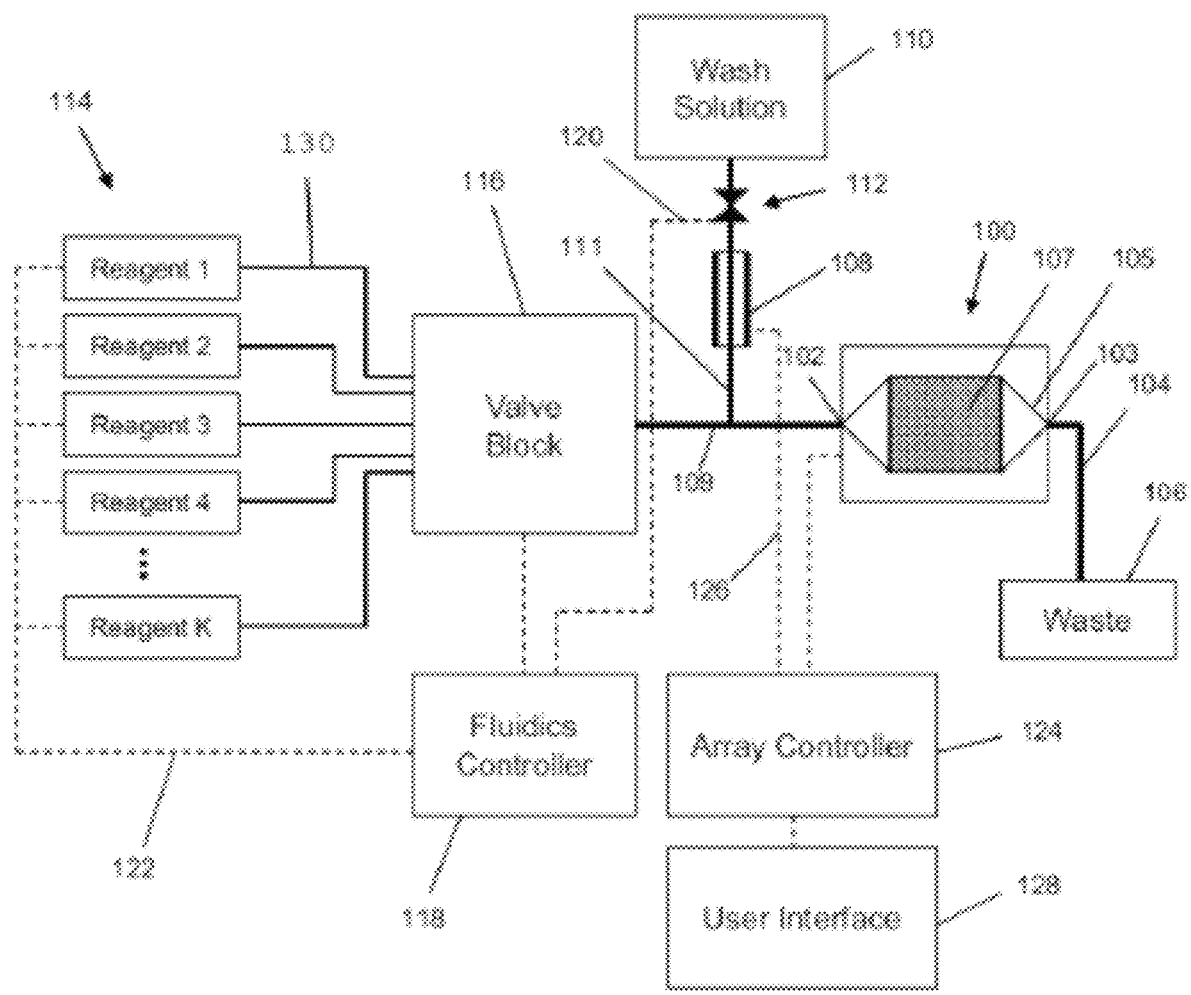
FIG. 1 is a block diagram illustrating components of an exemplary system for nucleic acid sequencing.

The following description and the various embodiments described herein are exemplary and explanatory only and are not to be construed as limiting or restrictive in any way. Other embodiments, features, objects, and advantages of the present teachings will be apparent from the description and accompanying drawings, and from the claims.

In accordance with various embodiments described, methods, systems, and kits that allow efficient preparation and/or identification of samples are provided. In some examples, the methods, systems, and kits may help increase throughput by allowing contemporaneous sequencing and/or analysis of multiple samples (e.g., multiplexed sequencing), facilitated by using sample discriminating codes or coded molecular constructs. Multiplexed sequencing may allow multiple coded samples (for example, different samples or samples from different sources) to be analyzed substantially simultaneously in a single sequencing run (e.g., on a common slide, chip, substrate, or other sample holder device) or substantially simultaneously during contemporaneous sequencing runs (e.g., on multiple slides, chops, substrates, or sample holders).

In some embodiments, the methods, systems, and kits disclosed allow for identification of an origin of samples used in multiplexed sequencing. Such identification may involve an analysis of sequencing data for the samples. The source of the sequencing data may be uniquely tagged, coded, or identified (e.g., to resolve a particular nucleic acid species associated with a particular sample population). Such identification may be facilitated by using unique sample discriminating codes or sequences (also known as barcodes, e.g., synthetic nucleic acid barcodes) that may be embedded within or otherwise associated with the samples. Use of sample discriminating codes is still subject to errors or misreads that may occur during sequencing. For example, an erroneous barcode read may alter interpretation of the barcode information, which may render the barcode unrecognizable and prevent correct sample identification. An erroneous barcode read may also result in the association of a sample to an incorrect sample source or population of origin.

Various disclosed embodiments, however, may mitigate the problem of detecting and/or correcting errors that can arise during the sequencing of samples comprising barcodes. For example, sample discriminating codes or sequences or barcodes and methodologies for developing robust sample discriminating codes or sequences or barcodes that incorporate an error-tolerant code (e.g., an error-correcting code or an error-detecting code) are provided.

Various disclosed embodiments may also generate a large number of potential barcodes that may be used to discriminate samples, for instance from one another, where these barcodes may also correspond to codewords that comprise an error-tolerant code (e.g., an error-correcting code or an error-detecting code). For instance, a sequencing instrument may receive signals when sequencing the generated barcodes, and the resultant signals received may represent a codeword of an error-tolerant code. In some embodiments, the large number of potential barcodes combined with the error-tolerant design of the barcodes may result in improvements to multiplexing, both in efficiency (e.g., number of simultaneous targets that can be sequenced), accuracy (e.g., error tolerance), and flexibility and customization of analysis.

Unless otherwise specifically designated herein, terms, techniques, and symbols of biochemistry, cell biology, cell and tissue culture, genetics, molecular biology, nucleic acid chemistry, and organic chemistry (including chemical and physical analysis of polymer particles, enzymatic reactions and purification, nucleic acid purification and preparation, nucleic acid sequencing and analysis, polymerization techniques, preparation of synthetic polynucleotides, recombinant techniques, etc.) used herein follow those of standard treatises and texts in the relevant field. See, e.g., Kornberg and Baker, DNA REPLICATION, 2nd ed. (W.H. Freeman, New York, 1992); Lehninger, BIOCHEMISTRY, 2nd ed. (Worth Publishers, New York, 1975); Strachan and Read, HUMAN MOLECULAR GENETICS, 2nd ed. (Wiley-Liss, New York, 1999); Birren et al. (eds.), GENOME ANALYSIS: A LABORATORY MANUAL SERIES (Vols. I-IV), Dieffenbach and Dveksler (eds.), PCR PRIMER: A LABORATORY MANUAL, and Green and Sambrook (eds.), MOLECULAR CLONING: A LABORATORY MANUAL (all from Cold Spring Harbor Laboratory Press); and Hermanson, BIOCONJUGATE TECHNIQUES, 2nd ed. (Academic Press, 2008).

As used herein, "amplifying" generally refers to performing an amplification reaction. As used herein, "amplicon" generally refers to a product of a polynucleotide amplification reaction, which includes a clonal population of polynucleotides, which may be single stranded or double stranded and which may be replicated from one or more starting sequences. In an example, the one or more starting sequences may be one or more copies of the same sequence, or they may be a mixture of different sequences that contain a common region that is amplified such as, for example, a specific exon sequence present in a mixture of DNA fragments extracted from a sample. Amplicons may also be formed by the amplification of a single starting sequence. Amplicons may be produced by a variety of amplification reactions whose products comprise replicates of one or more starting, or target, nucleic acids. Amplification reactions producing amplicons may be "template-driven" in that base pairing of reactants, either nucleotides or oligonucleotides, have complements in a template polynucleotide that are required for the creation of reaction products. Template-driven reactions may be primer extensions with a nucleic acid polymerase or oligonucleotide ligations with a nucleic acid ligase. Such reactions include, for example, polymerase chain reactions (PCRs), linear polymerase reactions, nucleic acid sequence-based amplifications (NASBAs), rolling circle amplifications, for example, or using rolling circle amplification to form a single body that may exclusively occupy a microwell as disclosed in Drmanac et al., U.S. Pat. Appl. Publ. No. 2009/0137404, which is incorporated by reference herein in its entirety. As used herein, "solid phase amplicon" generally refers to a solid phase support, such as a particle or bead, to which is attached a clonal population of nucleic acid sequences, which may have been produced by a emulsion PCR, for example.

As used herein, "analyte" generally refers to a molecule or biological sample that can directly affect an electronic sensor in a region (such as a defined space or reaction confinement region or microwell, for example) or that can indirectly affect such an electronic sensor by a by-product from a reaction involving such molecule or biological cell located in such region. In an embodiment, an analyte may be a sample or template nucleic acid, which may be subjected to a sequencing reaction, which may, in turn, generate a reaction by-product, such as one or more hydrogen ions, that can affect an electronic sensor. The term "analyte" may also encompass multiple copies of analytes, such as proteins, peptides, nucleic acids, for example, attached to solid supports, such as beads or particles. In an embodiment, an analyte may be a nucleic acid amplicon or a solid phase amplicon. A sample nucleic acid template may be associated with a surface via covalent bonding or a specific binding or coupling reaction, and may be derived from, for example, a shot-gun fragmented DNAamplicon library (which are examples of library fragments further discussed herein), or a sample emulsion PCR process creating clonally-amplified sample nucleic acid templates on particles such as Ion-Sphere™ particles. An analyte may include particles having attached thereto clonal populations of DNA fragments, e.g., genomic DNA fragments, cDNA fragments, for example.

As used herein, "primer" generally refers to an oligonucleotide, either natural or synthetic, that is capable, upon forming a duplex with a polynucleotide template, of acting as a point of initiation of nucleic acid synthesis and being extended from, for example, its 3' end along the template so that an extended duplex may be formed. Extension of a primer may be carried out with a nucleic acid polymerase, such as a DNA or RNA polymerase. The sequence of nucleotides added in the extension process may be determined by the sequence of the template polynucleotide. Primers may have a length in the range of from 14 to 40 nucleotides, or in the range of from 18 to 36 nucleotides, for example, or from N to M nucleotides where N is an integer larger than 18 and M is an integer larger than N and smaller than 36. Various embodiments may implement other suitable lengths for primers. Primers may be employed in a variety of amplification reactions, including linear amplification reactions using a single primer, or polymerase chain reactions, employing two or more primers, for example. Guidance for selecting the lengths and sequences of primers may be found in Dieffenbach and Dveksler (eds.), PCR PRIMER: A LABORATORY MANUAL, 2nd ed. (Cold Spring Harbor Laboratory Press, New York, 2003).

As used herein, "polynucleotide" or "oligonucleotide" generally refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, for example. Such monomers and their internucleosidic linkages may be naturally occurring or may be analogs thereof (e.g., naturally occurring or non-naturally occurring analogs). Example non-naturally occurring analogs may comprise PNAs, phosphorothioate internucleosidic linkages, bases containing linking groups permitting the attachment of labels, such as fluorophores, or haptens. In an embodiment, oligonucleotide may refer to (relatively) smaller polynucleotides, for example, having 5-40 monomeric units. Polynucleotides may, in some instances, include the natural deoxyribonucleosides (e.g., deoxyadenosine, deoxycytidine, deoxyguanosine, and deoxythymidine for DNA or their ribose counterparts for RNA) linked by phosphodiester linkages. However, they may also include non-natural nucleotide analogs (e.g., including modified bases, sugars, or internucleosidic linkages). In an embodiment, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes deoxythymidine, and that "I" denotes deoxyinosine, and "U" denotes deoxyuridine, unless otherwise indicated or implied from context. Whenever the use of an oligonucleotide or polynucleotide is associated with enzymatic processing, such as extension by a polymerase or ligation by a ligase, the oligonucleotides or polynucleotides in those instances may not contain certain analogs of internucleosidic linkages, sugar moieties, or bases at any or some positions. Unless otherwise noted the terminology and atom numbering conventions will follow those disclosed in Strachan and Read, HUMAN MOLECULAR GENETICS, 2nd ed. (Wiley-Liss, New York, 1999). Polynucleotides may range in size from a few monomeric units (e.g., 5-40), to several thousand monomeric units, for example.

As used herein, "defined space" (or "reaction space," which may be used interchangeably with "defined space") generally refers to any space or region (which may be in one, two, or three dimensions) in which at least some of a molecule, fluid, and/or solid can be confined, retained and/or localized. In various embodiments, the space may be a predetermined area (which may be a flat area) or volume, and may be defined, for example, by a depression or a micro-machined well in or associated with a microwell plate, microtiter plate, microplate, or a chip. The area or volume may also be determined based on an amount of fluid or solid, for example, deposited on an area or in a volume otherwise defining a space. For example, isolated hydrophobic areas on a generally hydrophobic surface may provide defined spaces. In an embodiment, a defined space may be a reaction chamber, such as a well or a microwell, which may be in a chip. In an embodiment, a defined space may be a substantially flat area on a substrate without wells, for example. A defined space may contain or be exposed to enzymes and reagents used in nucleotide incorporation.

As used herein, "reaction confinement region" or "reaction chamber" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest. In some embodiments, a reaction confinement region may include a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. In some embodiments, these latter types of reaction confinement regions may be referred to herein as microwells or reaction chambers, may be fabricated using any suitable microfabrication techniques, and may have volume, shape, aspect ratio (e.g., base width-to-well depth ratio), and other dimensional characteristics that may be selected depending on particular applications, including the nature of reactions taking place as well as the reagents, by-products, and labeling techniques (if any) that are employed. Reaction confinement regions may also be substantially flat areas on a substrate without wells, for example. In various embodiments, microwells may be fabricated using any suitable fabrication technique known in the art. Exemplary configurations (e.g., spacing, shape, and volume) of microwells or reaction chambers are disclosed in Rothberg et al., U.S. Pat. Publ. Nos. 2009/0127589 and 2009/0026082; Rothberg et al., U.K. Pat. Appl. Publ. No. GB 2461127; and Kim et al., U.S. Pat. No. 7,785,862, which are all incorporated by reference in their entirety.

Defined spaces or reaction confinement regions may be arranged as an array, which may be a substantially planar one-dimensional or two-dimensional arrangement of elements such as sensors or wells. The number of columns (or rows) of a two-dimensional array may or may not be the same. In some embodiments, the array comprises at least 100,000 chambers. Reaction chambers may have a horizontal width and a vertical depth that has an aspect ratio of about 1:1 or less, for example. In some embodiments, the pitch between the reaction chambers is no more than about 10 microns and each reaction chamber is no greater than 10 $\mu m^3$ (i.e., 1 pL) in volume, or no greater than 0.34 pL in volume, or no greater than 0.096 pL or, in some instances, 0.012 pL in volume. A reaction chamber may be $2^2$, $3^2$, $4^2$, $5^2$, $6^2$, $7^2$, $8^2$, $9^2$, or $10^2$ square microns in cross-sectional area at the top, for example. In some embodiments, the array may have at least $10^2$, $10^3$, $10^4$, $10^5$, $10^6$, $10^7$, $10^8$, $10^9$, or more reaction chambers, for example. The reaction chambers may be coupled to chemFETs.

Defined spaces or reaction confinement regions, whether arranged as an array or in some other configuration, may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement region, for example, may be represented as an electrical signal or a voltage, which may be digitalized (e.g., converted to a digital representation of the electrical signal or the voltage). In various embodiments, these measurements and representations may be considered raw data or a raw signal.

As used herein, "nucleic acid template" (or "sequencing template," which may be used interchangeably with "nucleic acid template") generally refers to a nucleic acid sequence that is a target of one or more nucleic acid sequencing reactions. A sequence for a nucleic acid template may comprise a naturally-occurring or synthetic nucleic acid sequence. A sequence for a nucleic acid template may also include a known or unknown nucleic acid sequence from a sample of interest. In various embodiments, a nucleic acid template may be attached to a solid support such as, e.g., a bead, microparticle, flow cell, or any other surface, support, or object.

As used herein, "fragment library" generally refers to a collection of nucleic acid fragments in which one or more fragments are used as a sequencing template. A fragment library may be generated in numerous ways (e.g., by cutting, shearing, restricting, or otherwise subdividing a larger nucleic acid into smaller fragments). Fragment libraries may be generated or obtained from naturally occurring nucleic acids, such as, for example, from bacteria, cancer cells, normal cells, =solid tissue, and the like. Libraries comprising synthetic nucleic acid sequences may also be generated to create a synthetic fragment library.

As used herein, a "molecular sample discriminating code" (or "molecular barcode," which may be used interchangeably with "molecular sample discriminating code") generally refers to an identifiable or resolvable molecular marker, which may be uniquely resolved and may be attached to a sample nucleic acid, biomolecule, or polymer, for example. Such a molecular sample discriminating code may be used for tracking, sorting, separating, and/or identifying sample nucleic acids, biomolecules, or polymers, and may be designed to have properties useful for manipulating nucleic acids, biomolecules, polymers, or other molecules. Molecular sample discriminating codes may comprise the same kind or type of material or subunits comprising the nucleic acid, biomolecule, or polymer they are intended to identify, or they may comprise one or more different material(s) or subunit(s). A molecular sample discriminating code may comprise a short nucleic acid comprising a known, predetermined, or designed sequence. A molecular sample discriminating code may be a nucleic acid sample discriminating code (or nucleic acid barcode), which may be an identifiable or resolvable nucleotide sequence (e.g., an oligonucleotide or polynucleotide sequence). Some example molecular sample discriminating codes may include one or more restriction endonuclease recognition sequences or cleavage sites, overhang ends, adaptor sequences, primer sequences, and the like (including combinations of features or properties). A molecular sample discriminating code may be a biopolymer sample discriminating code, which may include one or more antibody recognition sites, restriction sites, intra- or inert-molecule binding sites, and the like (including combinations of features or properties). A plurality of different molecular sample discriminating codes may be used to identify or characterize samples belonging to a common group, and may be attached to, coupled with, or otherwise associated with libraries (e.g., fragment libraries) of nucleic acids, biomolecules, polymers, or other molecules, for example. In various embodiments, a molecular sample discriminating code or molecular barcode may be represented by a sample discriminating code or sequence or barcode, which may comprise a set of symbols, components, or characters used to represent or define a molecular sample discriminating code or barcode. For example, a sample discriminating code or barcode may comprise a sequence of letters defining a known or predetermined sequence of nucleic acid bases or other biomolecule or polymer constituents. Other embodiments may implement any other suitable symbols and/or alphanumeric characters other than letters. Sample discriminating codes or barcodes may be used in a variety of sets, subsets, and groupings, for example as part of a sequencing run or in order to accomplish multiplexing. Sample discriminating codes or barcodes may be read, or otherwise recognized, identified, or interpreted as a function of a sequence or other arrangement or relationship of subunits that together form a code. In some embodiments, the sample discriminating codes may comprise a series of signals output by a sequencing instrument when sequencing the barcode according to a predetermined flow order (e.g., a flowspace over a barcode), as further detailed herein. In some embodiments, sample discriminating codes or barcodes may also contain one or more additional functional elements including key sequences for quality control and sample detection, primer sites, adaptors for ligation, linkers for attaching to substrates, inserts, and any other suitable elements.

FIG. 1 illustrates components of an exemplary system for nucleic acid sequencing that may be implemented with various embodiments. The components include a flow cell comprising a sensor array 100, a reference electrode 108, a plurality of reagents 114, a valve block 116, a wash solution 110, a valve 112, a fluidics controller 118, lines 120/122/126, passages 104/109/111, a waste container 106, an array controller 124, and a user interface 128. The flow cell and sensor array 100 includes an inlet 102, an outlet 103, a reaction chamber array 107, and a flow chamber 105 defining a flow path of reagents over the reaction chamber array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100.

In some embodiments, reagents 114 may, for example, contain dNTPs to be flowed through passages 130 and through the valve block 116, which may control the flow of the reagents 114 to flow chamber 105 via passage 109. The system may include a reservoir 110 for containing a wash solution that may be used to wash away dNTPs, for example, that may have previously been flowed. The reaction chamber array 107 may include an array of defined spaces or reaction confinement regions, such as wells or microwells, for example, that is operationally associated with a sensor array so that, for example, each reaction chamber has a sensor suitable for detecting an analyte or reaction property of interest. The reaction chamber 107 may be integrated with the sensor array as a single device or chip. The flow cell may have a variety of designs for controlling the path and flow rate of reagents over the reaction chamber array 107, and may be a microfluidics device. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls.

In some embodiments, the system may be configured to let a single fluid or reagent contact the reference electrode 108 throughout a multi-step reaction. The valve 112 may be shut to prevent wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between the reference electrode 108 and the junction between passages 109 and 111 may be selected so that little or no amount of the reagents flowing in passage 109 and possibly diffusing into passage 111 reach the reference electrode 108. In an embodiment, the wash solution 110 may be selected as being in continuous contact with the reference electrode 108. In an example, such a configuration may be useful for multi-step reactions using frequent wash steps. In various embodiments, the fluidics controller 118 may be programmed to control driving forces for flowing reagents 114 and the operation of valve 112 and valve block 116 with any suitable instrument control software, such as LabView (National Instruments, Austin, Tex.), to deliver reagents to the flow cell and sensor array 100 according to a predetermined reagent flow ordering. The reagents may be delivered for predetermined durations, at predetermined flow rates, and may measure physical and/or chemical parameters providing information about the status of one or more reactions taking place in defined spaces or reaction confinement regions, such as, for example, wells or microwells.

Figure 2A:
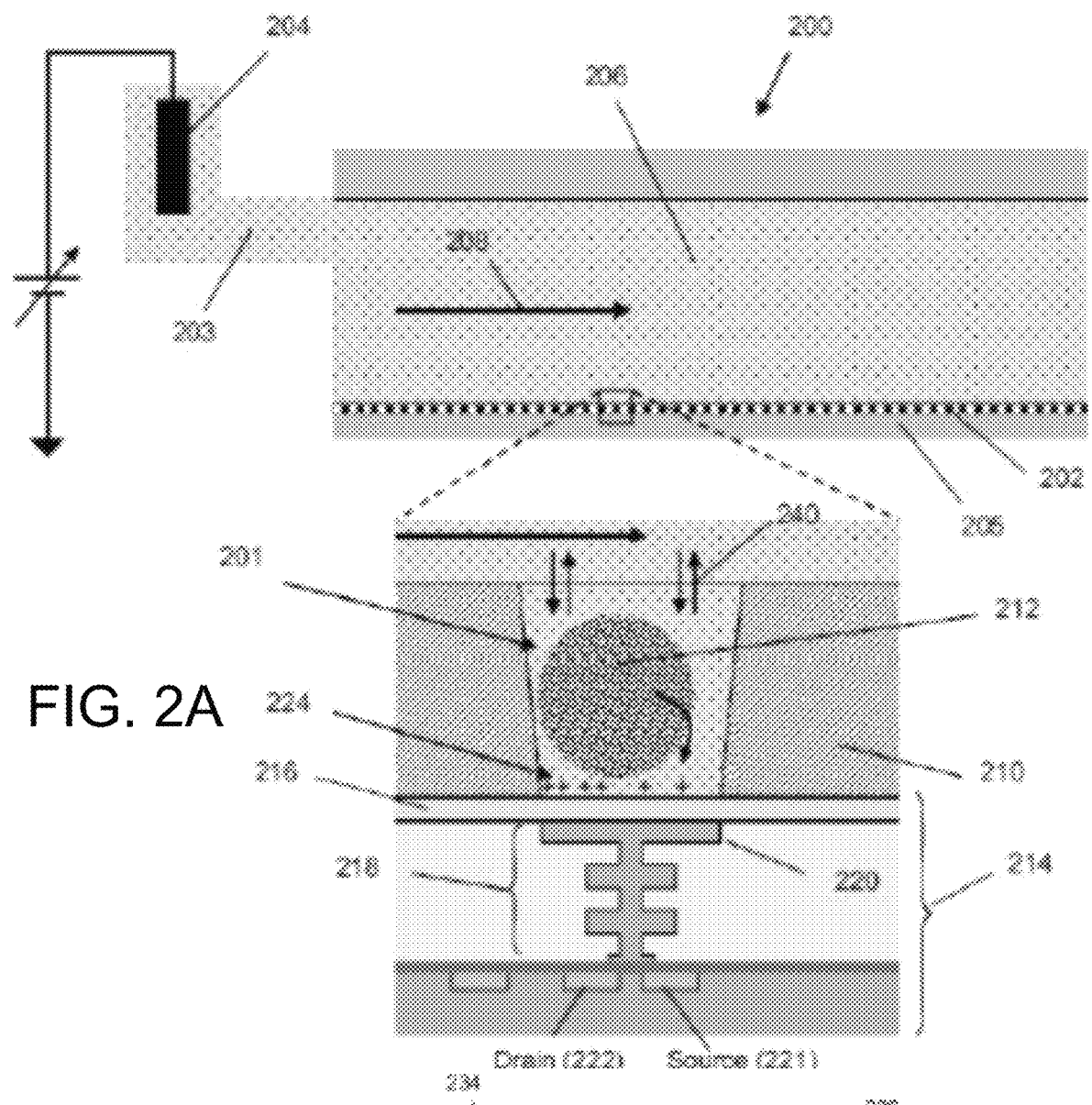
FIG. 2A illustrates cross-sectional and detailed views of an exemplary flow cell for nucleic acid sequencing.

FIG. 2A illustrates cross-sectional and detailed views of an exemplary flow cell 200 for nucleic acid sequencing in accordance with various embodiments. The flow cell 200 may include a reaction chamber array 202, a sensor array 205, and a flow chamber 206 in which a reagent flow 208 may move across a surface of the reaction chamber array 202, over open ends of a reaction chamber. The flow of reagents (e.g., nucleotide species) can be provided in any suitable manner, including delivery by pipettes, or through tubes or passages connected to a flow chamber. The duration, concentration, and/or other flow parameters may be the same or different for each reagent flow. Likewise, the duration, composition, and/or concentration for each wash flow may be the same or different.

A reaction chamber 201 in the reaction chamber array 202 may have any suitable volume, shape, and aspect ratio, which may be selected depending on one or more of any reagents, by-products, and labeling techniques used, and the reaction chamber 201 may be formed in layer 210, for example, using any suitable fabrication or microfabrication technique. A reaction chamber may be in the form of a well, a microwell, a throughhole, surface portion having relative liquid affinity to act as a confinement region, or any other suitable containment structure. A sensor 214 in the sensor array 205 may be an ion sensitive (ISFET) or a chemical sensitive (chemFET) sensor with a floating gate 218 having a sensor plate 220 separated from the reaction chamber interior by a passivation layer 216, and may be responsive to (and generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage output signal. Reactants, wash solutions, and other reagents may move into reaction chamber, for instance by diffusion 240. One or more analytical reactions to identify or determine characteristics or properties of an analyte of interest may be carried out in one or more reaction chamber of the reaction chamber array 202.

In some embodiments, such reactions generate, directly or indirectly, by-products that affect the amount of charge 224 in sensing proximity of (e.g., adjacent to) the sensor plate 220. In an embodiment, a reference electrode 204 may be fluidly connected to the flow chamber 206 via a flow passage 203. In an embodiment, the reaction chamber array 202 and the sensor array 205 may together form an integrated unit forming a bottom wall or floor of the flow cell 200. In an embodiment, one or more copies of an analyte may be attached to a solid phase support 212, which may include microparticles, nanoparticles, beads, gels, and may be solid and porous, for example. The analyte may include a nucleic acid analyte, including a single copy and multiple copies, and may be made, for example, by rolling circle amplification (RCA), exponential RCA, or other suitable techniques to produce an amplicon without the need of a solid support.

Figure 2B:
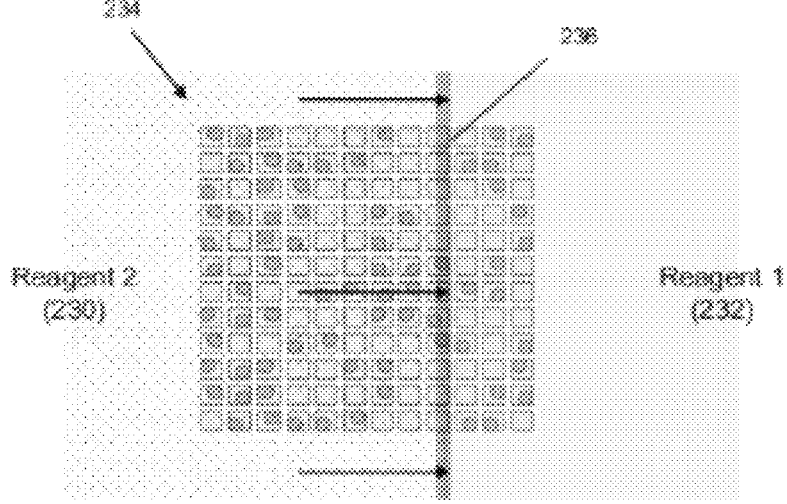
FIG. 2B illustrates an exemplary uniform flow front between successive reagents moving across a section of an exemplary reaction chamber array.

FIG. 2B illustrates an exemplary uniform flow front between successive reagents moving across a section 234 of an exemplary reaction chamber array in accordance with various embodiments. A "uniform flow front" between first reagent 232 and second reagent 230 may refer to the reagents undergoing little or no mixing as they move, thereby keeping a boundary 236 between them narrow. The boundary may be linear for flow cells having inlets and outlets at opposite ends of their flow chambers, or it may be curvilinear for flow cells having central inlets (or outlets) and peripheral outlets (or inlets). In an embodiment, the flow cell design and reagent flow rate may be selected so that each newly introduced reagent flows with a uniform flow front as it transits the flow chamber during a switch from one reagent to another.

Figure 3:
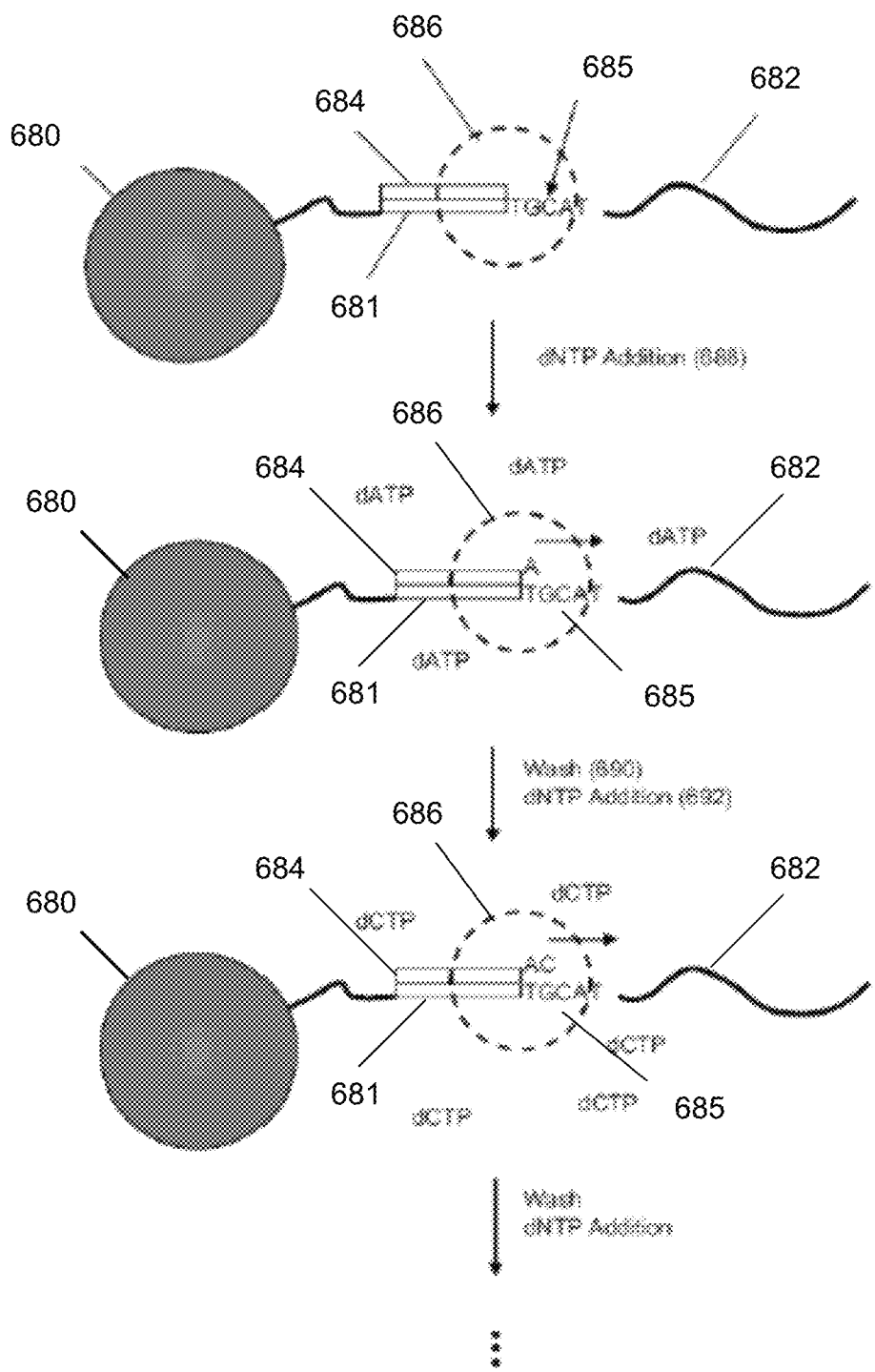
FIG. 3 illustrates an exemplary process for label-free, pH-based sequencing.

FIG. 3 illustrates an exemplary process for label-free, pH-based sequencing in accordance with various embodiments. A template 682 with sequence 685 and a primer binding site 681 are attached to a solid phase support 680. The template 682 may be attached as a clonal population to a solid support, such as a microparticle or bead, for example, and may be prepared as disclosed in Leamon et al., U.S. Pat. No. 7,323,305, which is incorporated by reference herein in its entirety. In an embodiment, the template may be associated with a substrate surface or present in a liquid phase with or without being coupled to a support. A primer 684 and DNA polymerase 686 are operably bound to the template 682. As used herein, "operably bound" generally refers to a primer being annealed to a template so that the primer's 3' end may be extended by a polymerase and that a polymerase is bound to such primer-template duplex (or in close proximity thereof) so that binding and/or extension may take place when dNTPs are added.

In step 688, dNTP (shown as dATP) is added, and the DNA polymerase 686 incorporates a nucleotide "A" (since "T" is the next nucleotide in the template 682 and is complementary to the flowed dATP nucleotide). In step 690, a wash is performed in accordance with descriptions presented herein. In step 692, the next dNTP (shown as dCTP) is added, and the DNA polymerase 686 incorporates a nucleotide "C" (since "G" is the next nucleotide in the template 682). The pH-based nucleic acid sequencing, in which base incorporations may be determined by measuring hydrogen ions that are generated as natural by-products of polymerase-catalyzed extension reactions, may be performed using at least in part one or more features of Anderson et al., A SYSTEM FOR MULTIPLEXED DIRECT ELECTRICAL DETECTION OF DNA SYNTHESIS, Sensors and Actuators B: Chem., 129:79-86 (2008); Rothberg et al., U.S. Pat. Appl. Publ. No. 2009/0026082; and Pourmand et al., DIRECT ELECTRICAL DETECTION OF DNA SYNTHESIS, Proc. Natl. Acad. Sci., 103:6466-6470 (2006), which are all incorporated by reference herein in their entirety. In an embodiment, after each addition of a dNTP, an additional step may be performed in which the reaction chambers are treated with a dNTP-destroying agent, such as apyrase, to eliminate any residual dNTPs remaining in the chamber that might result in spurious extensions in subsequent cycles.

In an embodiment, the primer-template-polymerase complex may be subjected to a series of exposures of different nucleotides in a predetermined or known sequence or ordering. When one or more nucleotides are incorporated, then the signal resulting from the incorporation reaction may be detected, and after repeated cycles of nucleotide addition, primer extension, and signal acquisition, the nucleotide sequence of the template strand may be determined. In an example, the output signals measured throughout this process depend on the number of nucleotide incorporations. In particular, in each additional sequencing step, the polymerase extends the primer by incorporating added dNTP when the next base in the template is complementary to the added dNTP. If there is one complementary base, there is one incorporation; if two, there are two incorporations; if three, there are three incorporations, and so on. With each incorporation, a hydrogen ion is released, and collectively a population of released hydrogen ions changes the local pH of the reaction chamber.

In an embodiment, the production of hydrogen ions may be monotonically related to the number of contiguous complementary bases in the template (as well as to the total number of template molecules with primer and polymerase that participate in an extension reaction). Thus, when there is a number of contiguous identical complementary bases in the template (which may represent a homopolymer region), the number of hydrogen ions generated and thus the magnitude of the local pH change is proportional to the number of contiguous identical complementary bases (and the corresponding output signals are then sometimes referred to as "1-mer," "2-mer," "3-mer" output signals, etc.). If the next base in the template is not complementary to the added dNTP, then no incorporation occurs and no hydrogen ion is released (and the output signal is then sometimes referred to as a "0-mer" output signal). In some examples, in each wash step of the cycle, an unbuffered wash solution at a predetermined pH may be used to remove the dNTP of the previous step in order to prevent misincorporations in later cycles. Deliveries of nucleotides to a reaction vessel or chamber may be referred to as "flows" of nucleotide triphosphates (or dNTPs). For convenience, a flow of dATP will sometimes be referred to as "a flow of A" or "an A flow," and a sequence of flows may be represented as a sequence of letters, such as "ATGT" indicating "a flow of dATP, followed by a flow of dTTP, followed by a flow of dGTP, followed by a flow of dTTP."

In an embodiment, the four different kinds of dNTP are added sequentially to the reaction chambers, so that each reaction is exposed to the four different dNTPs, one at a time. In an embodiment, the four different kinds of dNTP are added in the following sequence: dATP, dCTP, dGTP, dTTP, dATP, dCTP, dGTP, dTTP, etc., with the exposure, incorporation, and detection steps followed by a wash step. The exposure to a nucleotide followed by a washing step can be considered a "nucleotide flow." In some examples, four consecutive nucleotide flows can be considered a "cycle." For example, a two cycle nucleotide flow order can be represented by: dATP, dCTP, dGTP, dTTP, dATP, dCTP, dGTP, dTTP, with each exposure being followed by a wash step. Different flow orders may be implemented, as further detailed herein. In various embodiments, the predetermined sequence or ordering may be based on a cyclical, repeating pattern of consecutive repeats of a predetermined reagent flow ordering (e.g., consecutive repeats of predetermined sequence of four nucleotide reagents such as "TACG TACG . . . "), or may be based on a random reagent flow ordering, or may be based on an ordering comprising in whole or in part a phase-protecting reagent flow ordering as described in Hubbell et al., U.S. patent application Ser. No. 13/440,849, published Oct. 28, 2012 as U.S. Patent Pub. No. 2012/0264621, entitled PHASE-PROTECTING REAGENT FLOW ORDERINGS FOR USE IN SEQUENCING-BY-SYNTHESIS, which is incorporated by reference herein in its entirety, or some combination thereof. In other embodiments, labeled pH-based sequencing may be implemented in a similar manner.

Figure 4:
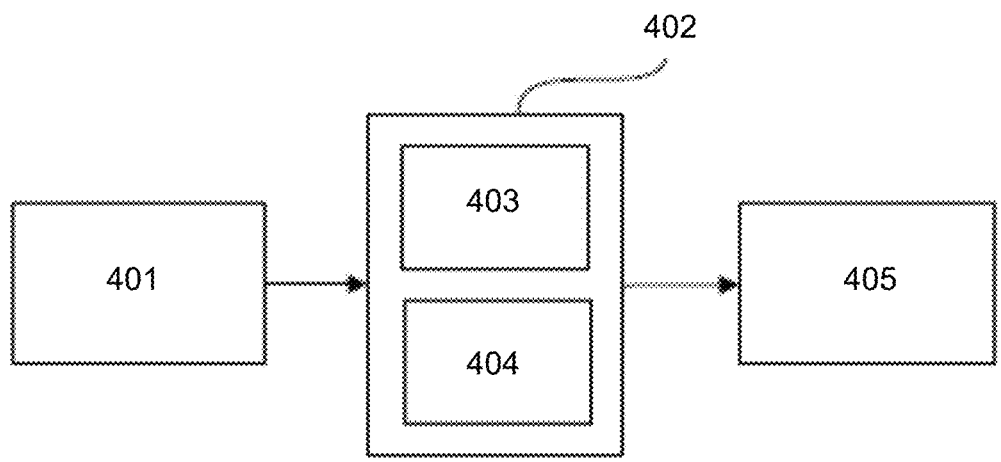
FIG. 4 is a block diagram illustrating an exemplary system for obtaining, processing, and/or analyzing multiplex nucleic acid sequencing data.

FIG. 4 illustrates an exemplary system for obtaining, processing, and/or analyzing multiplex nucleic acid sequencing data in accordance with various exemplary embodiments. The system includes a sequencing instrument 601, a server 402, and one or more end user computers 405. The sequencing instrument 401 may be configured to process samples comprising barcodes and to deliver reagents according to a predetermined ordering as detailed herein. The predetermined ordering may be based on a cyclical, repeating pattern of consecutive repeats of a predetermined reagent flow ordering (e.g., consecutive repeats of predetermined sequence of four nucleotide reagents such as "TACG TACG . . . "), or may be based on a random reagent flow ordering, or may be based on an ordering comprising in whole or in part a phase-protecting reagent flow ordering, or some combination thereof. In an embodiment, the barcodes may be determined at least in part as a function of the ordering. For example, the barcodes may comprise flow-space designed barcodes that are designed in accordance with a predetermined flow ordering, as further described herein. Exemplary sequencing instruments that can be used in conjunction with the barcodes of the present disclosure include, but are not limited to, for example, Ion PGM™, Ion Proton™, Ion S5™ and Ion S5 XL Next Generation™ Sequencing System. Persons having ordinary skill in the art would appreciate that other sequencing instruments and platforms, such as, for example, various fluorophore-labeled nucleotide sequencing platforms, also may be used in conjunction with the barcodes of the present disclosure.

The server 402 may include a processor 403 and a memory and/or database 404. The sequencing instrument 401 and the server 402 may include one or more computer readable media for obtaining, processing, and/or analyzing multiplex nucleic acid sequencing data. In an embodiment, the instrument and the server or other computing means or resource may be configured as a single component. One or more of these components may be used to perform all or parts the embodiments described herein.

In some embodiments, the barcodes according to the present disclosure comprise codewords of an error-tolerant code, where the codewords are represented in flowspace (e.g., comprise digits, characters, or some other symbols corresponding to numbers of nucleotide incorporations responsive to predetermined nucleotide flows) rather than in base space.

In various exemplary embodiments, a sequence may be determined and/or one or more nucleic acid samples may be identified using sequencing-by-synthesis. In sequencing-by-synthesis, the sequence of a target nucleic acid may be determined by the stepwise synthesis of complementary nucleic acid strands on a target nucleic acid (whose sequence and/or identity is to be determined) serving as a template for the synthesis reactions (e.g., by a polymerase extension reaction that typically includes the formation of a complex comprising a template (or target polynucleotide), a primer annealed thereto, and a polymerase operably coupled or associated with the primer-template hybrid so as to be capable of incorporating a nucleotide species (e.g., a nucleoside triphosphate, a nucleotide triphosphate, a precursor nucleoside or nucleotide) to the primer). During sequencing-by-synthesis, nucleotides may be sequentially added to growing polynucleotide molecules or strands at positions complementary to template polynucleotide molecules or strands. The addition of the nucleotides to the growing complementary strands, which may be detected using a variety of methods (e.g., pyrosequencing, fluorescence detection, and label-free electronic detection, and the like), may be used to identify the sequence composition of the template nucleic acid. This process may be iterated until a complete or selected sequence length complementary to the template has been synthesized.

As noted above, in various embodiments, data and signals that may be generated, processed, and/or analyzed may be obtained using electronic or charged-based nucleic acid sequencing. In electronic or charged-based sequencing (e.g., pH-based sequencing), a nucleotide incorporation event may be determined by detecting ions (e.g., hydrogen ions) generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, or the like. The sample or template nucleic acid may be operably associated to a primer and polymerase and may be subjected to repeated cycles or "flows" of deoxynucleoside triphosphate ("dNTP") addition and washing. The primer may be annealed to the sample or template so that the primer's 3' end can be extended by a polymerase whenever dNTPs complementary to the next base in the template are added. Based on the known sequence of flows and on measured signals indicative of ion concentration during each nucleotide flow, the identity of the type, sequence and number of nucleotide(s) associated with a sample nucleic acid present in a reaction chamber can be determined.

Figure 5:
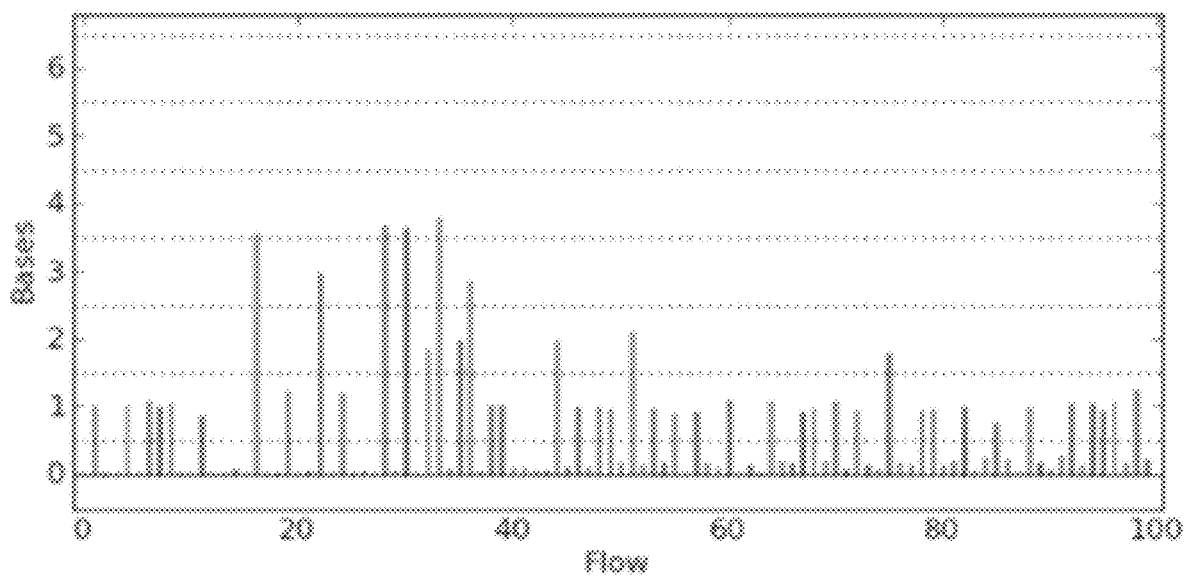
FIG. 5 shows an exemplary ionogram representation of signals from which base calls may be made.

FIG. 5 shows an exemplary ionogram representation of signals from which base calls may be made. In this example, the x-axis shows the nucleotide that is flowed and the corresponding number of nucleotide incorporations may be estimated by rounding to the nearest integer shown in the y-axis, for example. Signals used to make base calls and determine sequencing data (e.g., a flowspace vector) may be from any suitable point in the acquisition or processing of the data signals received from sequencing operations. For example, the signals may be raw acquisition data or data having been processed (e.g., by background filtering, normalization, correction for signal decay, and/or correction for phase errors or effects, and the like). The base calls may be made by analyzing any suitable signal characteristics (e.g., signal amplitude, intensity, and the like).

In various embodiments, output signals due to nucleotide incorporation may be further processed, given knowledge of the predetermined nucleotide species that were flowed and in what order to obtain such signals, to make base calls for the flows and compile consecutive base calls associated with a sample nucleic acid template into a read. A base call refers to a particular nucleotide identification (e.g., dATP ("A"), dCTP ("C"), dGTP ("G"), or dTTP ("T")). Base calling may include performing one or more signal normalizations, signal phase and signal droop (e.g, enzyme efficiency loss) estimations, and signal corrections, and may identify or estimate base calls for each flow for each defined space. Base calling may include performing or implementing one or more of the teachings disclosed in Davey et al., U.S. patent application Ser. No. 13/283,320, published May 3, 2012 as U.S. Patent Pub. No. 2012/0109598, entitled PREDICTIVE MODEL FOR USE IN SEQUENCING-BY-SYNTHESIS, which is incorporated by reference herein in its entirety. Other aspects of signal processing and base calling may include performing or implementing one or more of the teachings disclosed in Davey et al., U.S. patent application Ser. No. 13/340,490, published Jul. 5, 2012 as U.S. Patent Pub. No. 2012/0173159, entitled METHOD, SYSTEM, AND COMPUTER READABLE MEDIA FOR NUCLEIC ACID SEQUENCING, and Sikora et al., U.S. patent application Ser. No. 13/588,408, published Mar. 7, 2013 as U.S. Patent Pub. No. 2013/0060482, entitled METHOD, SYSTEM, AND COMPUTER READABLE MEDIA FOR MAKING BASE CALLS IN NUCLEIC ACID SEQUENCING, which are all incorporated by reference herein in their entirety.

FIGS. 6A and 6B demonstrate a relationship between a base space sequence and a flowspace vector. A series of signals (e.g., produced by flowing dNTPs in the presence of a polynucleotide) representative of a number of incorporations (e.g., incorporations of flowed dNTPS into the polynucleotide) or lack thereof (e.g., 0-mer, 1-mer, 2-mer, etc.) may be referred to as a flowspace vector. sequence, or string. In an embodiment, a flowspace vector, sequence, or string may comprise of a series of symbols (e.g., 0, 1, 2, 3, and the like) representative of incorporations. When a predetermined flow order is known in combination with a flowspace vector, a translation to base space may be produced. For example, given the number of incorporations (e.g., 0, 1, 2 or 3) and the particular dNTP flowed (e.g., A, G, T, C), the translated base space may comprise a base complementary to the flowed and incorporated dNTP, where a consecutive number of repeating bases may correspond to the number of incorporations indicated by the flowspace vector (e.g., 2 or more).

In an embodiment, the flowspace vector may be produced using any suitable nucleotide flow ordering, including a predetermined ordering based on a cyclical, repeating pattern of consecutive repeats of a predetermined reagent flow ordering, based on a random reagent flow ordering, or based on an ordering comprising in whole or in part a phase-protecting reagent flow ordering, or some combination thereof. In FIGS. 6A and 6B, an exemplary base space sequence AGTCCA is subjected to sequencing operations using a cyclical flow ordering of TACG. The flows result in a series of signals having an amplitude (e.g., signal intensity) related to the number of nucleotide incorporations (e.g., 0-mer, 1-mer, 2-mer, etc.). This series of signals generates the flowspace vector 101001021. As shown in FIG. 6A, the base space sequence AGTCCA may be translated to a flowspace vector 101001021 under a cyclical flow ordering of TACG . . . . As shown in FIG. 6B and detailed herein, the flowspace vector may be mapped back to the base space sequence associated with the sample given a predetermined flow ordering.

Barcodes

In various embodiments, sample discriminating codes or barcodes may comprise or correspond to or with (whether directly or indirectly) sequences of nucleotides, biomolecule components and/or subunits, or polymer components and/or subunits. In an embodiment, a sample discriminating code or barcode may correspond to a sequence of individual nucleotides in a nucleic acid or subunits of a biomolecule or polymer or to sets, groups, or continuous or discontinuous sequences of such nucleotides or subunits. In an embodiment, a sample discriminating code or barcode may also correspond to or with (whether directly or indirectly) transitions between nucleotides, biomolecule subunits, or polymer subunits, or other relationships between subunits forming a sample discriminating code or barcode (e.g., adaptors, key bases, and the like).

In various embodiments, sample discriminating codes or barcodes may have properties that permit them to be sequenced, or otherwise recognized, identified, or interpreted with improved accuracy and/or reduced error rates for a given code type, length, or complexity. In an embodiment, a sample discriminating code or barcode may be designed as a set (which may include subsets) of individual sample discriminating codes or barcodes. In some embodiments, one or more sample discriminating codes or barcodes in a set (or in a subset from that set) may be selected based on one or more criteria to improve accuracy and/or reduce error rates in reading, or otherwise recognizing, identifying, discriminating, or interpreting the codes.

In various embodiments, sample discriminating codes or barcodes may be designed to exhibit high fidelity reads, which may be assessed based on empirical sequencing measurements. The level of fidelity may be based on predictions of the read accuracy of a sample discriminating code or barcode having a particular nucleotide sequence. Certain nucleotide sequences known to cause sequencing read ambiguity, errors, or sequencing bias may be avoided. Design may be based on accurately calling the sample discriminating code or barcode (and associated sample or nucleic acid population), even in the presence of one or more errors. In various embodiments, fidelity may be based on the probability of correctly sequencing the sample discriminating code or barcode, which may be at least 82%, or at least 85%, or at least 90%, or at least 95%, or at least 99%, or more.

In various embodiments, sample discriminating codes or barcodes may be designed to exhibit improved read accuracy for sequencing using a sequence-by-synthesis platform (as discussed previously), which may include fluorophore-labeled nucleotide sequencing platforms or non-labeled sequencing platforms, such as, for example, the Ion PGM™ and Ion Proton™ Sequencers, and the Ion S5™ and Ion S5 XL Next Generation™ Sequencing System. Design of the sample discriminating codes or barcodes and specific sequences are not limited to any particular instrument platform or sequencing technology, however. In the case of non-nucleic acid codes, sample discriminating codes or barcodes may be sequences, identified, interpreted or otherwise recognized using methods known in the art, including for example, amino acid sequencing for protein sample discriminating codes.

In various embodiments, a design approach may include applying a series of sample discriminating code or barcode constraints or criteria to achieve desired properties or performance. Such constraints or criteria may include one or more of uniqueness of nucleic acid barcode sequences and a degree of separation from other nucleic acid barcode sequences. A set of barcodes may be a nested set of barcodes, which may be based on one or more design criteria. In an embodiment, nested barcode sets may be designed analogously to Matryoshka nesting, such that the properties of a subset are entirely contained within the properties of a genus set. For example, a first subset of barcodes meeting certain properties (e.g., a high sequencing fidelity) may be selected from a larger set of barcodes meeting the same properties. For example, if a set of barcodes comprises 96 uniquely identifiable barcodes, then a subset of 16 barcodes may be selected from the 96 available barcodes for a sequencing experiment comprises only 16 multiplexed samples. The subset of 16 barcodes may thus be optimized to a similar degree as a larger subset of 32 barcodes or 48 barcodes selected from the full set of 96 barcodes. In an embodiment, the barcodes may be designed as an ordered list of nested barcodes. In an embodiment, the barcodes (e.g., a set of 96) may be ordered by having a first barcode, a second barcode that is the one (of the remaining 95) that is furthest from the first one under a suitable distance measure, a third barcode that is the one (of the remaining 94) that is furthest from the first and second one under a suitable distance measure, and so on until the barcodes have been ordered.

In various embodiments, sample discriminating codes or barcodes may be bound to a target sequence, and in such cases may assist in uniquely identifying or discriminating different target sequences. The target sequence may be any type of sequence from any source of interest, including amplicons, candidate genes, mutational hot spots, single nucleotide polymorphisms, genomic library fragments, etc., for example. The sample discriminating code or barcode sequence may be operatively coupled to the target sequence at any of various points in the sample preparation process using techniques such as PCR amplification, DNA ligation, bacterial cloning, etc., for example. The sample discriminating code or barcode sequence may be contained in oligonucleotides and ligated to genomic library fragments using any suitable DNA ligation technique.

In various embodiments, sample discriminating codes or barcodes may have various lengths. For example, lengths for sample barcodes may be selected based on a number of samples to be identified. In various embodiments, for a 16-sample multiplexed sequencing experiment, 16 uniquely identifiable barcodes may be sufficient to uniquely identify each sample. Similarly, for a 64- or 96-sample multiplexed sequencing experiment, for example, 64 or 96 barcodes may be sufficient, respectively.

Some configurations may leverage longer codes, or larger barcodes, in order to achieve larger multiplex numbers. Although longer barcodes will allow identification of a larger number of samples, in some instance these longer barcodes may have drawbacks. For example, in sequencing-by-synthesis, longer barcodes may require additional nucleotide flows, which may decrease accuracy given that sequencing tends to be maximally accurate in earlier flows. In addition, where a sequencing system has a length criteria (e.g., 200 base pairs) longer barcodes may take up more sequencing real estate. As such, the target fragments appended to the barcodes may be required to meet a smaller length criteria (e.g., the longer barcodes may be more practical to use to sequence shorter targets).

In various embodiments, sample discriminating codes or barcodes may be designed based on one or more criteria set forth above (which may be taken alone or in combination). Various combinations of criteria may be chosen based on the sequencing experiment. For example, if barcodes are to be used for a small number of samples, the barcodes may not necessarily be designed to have nested subsets. The design criteria may be selected based on the number of samples, the level of accuracy desired, the sensitivity of the sequencing instrument to detect individual samples, the accuracy of the sequencing instrument, and the like.

In various embodiments, sample discriminating codes or barcodes as set forth herein may be used in any suitable manner to assist in identifying or resolving samples. For example, barcodes may be used individually, or two or more barcodes may be used in combination. In an embodiment, a single barcode may identify one target sequence or multiple target sequences. For example, a single barcode may identify a group of target sequences. A barcode may be read separately from the target sequence or as part of a larger read operation spanning the barcode and a target sequence. The barcode may be positioned at any suitable position within the sample, including before or after a target sequence.

Barcode Design & Flowspace

In various embodiments, sample discriminating codes or barcodes may be designed based on a flowspace. In other words, the barcode may be designed based at least partly on flowspace vectors (e.g., as a function of flow order). For example, sample discriminating codes or barcodes may be designed based on projection into flowspace as a flowspace vector under a selected or predetermined nucleotide flow ordering. In another example, a series of flowspace vectors may be generated that can then be translated into base space (e.g., according to a predetermined flow ordering) in order to produce the barcode sequences.

In an embodiment, a flowspace vector of a barcode may comprise a string of symbols (e.g., a string of digits or characters such as 0, 1, 2, and so on, that may respectively represent a non-incorporation, a 1-mer incorporation, a 2-mer incorporation, and so on), responsive to flows of nucleotide flowed or introduced according to a predetermined ordering. In various embodiments, the flowspace string or vector may represent or correspond to a codeword of an error-tolerant code (e.g., an error-correcting code). In an error-correcting code, a string of characters may be such that errors introduced into the string (e.g., during sequencing) can be detected and/or corrected based on remaining characters in the string. An error-correcting code may be made up of a set of different character strings, which may be referred to as codewords, over a given finite alphabet $\Sigma$ of character elements. A codeword may be viewed as comprising a message plus some redundant data or parity data allowing a decoder to correctly decode a codeword containing one or more errors. Codewords may be designed to be sufficiently separated from one another to allow for a permissible numbers of errors to be detected in the transmission of a codeword and, in some cases, to be corrected by calculating which actual codeword is closest to the received codeword.

In various embodiments, sample discriminating codes or barcodes may be designed using any suitable type of error-correcting code. The error-correcting code may be a linear block code using an alphabet $\Sigma$ of character elements with each codeword having n encoding character elements. Redundancy and/or parity data may be added to a message (e.g., subset of the codeword) to allow a receiver to detect and/or correct errors in a transmitted codeword, and to recover the original message using a suitable decoding algorithm. In sequencing-by-synthesis, for example, a message string may be considered "transmitted" when a barcode has been sequenced and projected into flowspace as a flowspace string.

In various embodiments, sample discriminating codes or barcodes may be designed using various numbers of character elements in a code alphabet, which may vary according to a particular application. The error-correcting code may be a binary code using an alphabet of two character elements. The error-correcting code may be a ternary code using an alphabet of three character elements. In an embodiment, the number of characters elements may depend on a length of a longest homopolymer run allowed in the barcode sequence. For example, if a barcode has only 1-mers (no repeating bases), then the error-correcting code may be a binary code with one character to represent a non-incorporation and another character to represent a single-base incorporation (e.g., an alphabet $\Sigma$ for such a binary code may be {0, 1}). In another example, if the barcode has only 1-mers and 2-mers, then the error-correcting code may be a ternary code with the same non-incorporation and single-base incorporation characters, and a third character to represent a two-base incorporation (e.g., an alphabet $\Sigma$ for such a ternary code may be {0, 1, 2}). The size and the set of characters used in other code alphabets may be suitably modified if the barcode sequence has 3-mers, 4-mers, and so on.

In various embodiments, sample discriminating codes or barcodes may be designed using an error-correcting code based at least in part on Hamming codes, Golay codes, and/or tetracode codes. In an embodiment, the error-correcting code may be a binary Hamming code, a binary Golay code, ternary Hamming code, a ternary Golay code, and/or any other suitable code. See, e.g., Hoffman et al., Coding Theory: The Essentials, Marcel Dekker, Inc. (1991); and Lin et al., Error Control Coding: Fundamentals And Applications, Prentice Hall, Inc. (1983).

In various embodiments, sample discriminating codes or barcodes may be designed to have error-tolerant properties expressed in flowspace. In other words, sequencing errors may be related to incorrect digits or characters in the flowspace representation of the barcode according to a predetermined flow order (e.g., an erroneous "0" or "0-mer" present where a "1" or "1-mer" should be in the flowspace representation). For example, a 1-base (in flowspace) error-tolerant barcode set may be designed such that if a sequencing error is encountered at any position in the flowspace representation in one or more barcodes of the set, each barcode may still be resolvable from other barcodes in the set because their flowspace representations all differ from the flowspace representation of the erroneous barcode(s) in at least two digit locations; in this way, if the error occurred at one of these two digit locations, the other remains available to allow distinction between the barcodes. The set may also be designed to enable distinguishing barcodes within it even where there are multiple errors in flowspace (e.g., 2, 3, etc.). Such error-tolerant properties may help provide a higher degree of confidence (e.g., accuracy) when resolving complex multiplexed samples in the presence of potential sequencing errors. Candidate barcodes in a set may be compared to ascertain error-tolerant properties in flowspace. For example, such barcodes can be compared (e.g., via computer analysis or simulation) to determine whether, if any one error in flowspace (or 2, 3, etc., as the criterion may be) occurred, the codes can still be distinguished. In another example, candidate flowspace codewords (e.g., that translate to candidate barcode sequences according to a predetermined flow order) can be compared to ascertain the error-tolerant properties.

Various algorithms and/or software tools may be used to assist in the generation of error-correcting codes. A number of different design considerations may factor into the development of a coding strategy. As explained herein, a barcode sequence and a flowspace codeword have a mapping relationship to each other for a given flow ordering. Thus, design or selection criteria with respect to the barcode sequence may be translated into corresponding design/selection criteria for the flowspace coding. Likewise, design/selection criteria with respect to the flowspace coding may be translated into corresponding design/selection criteria for the barcode sequence.

In various embodiments, sample discriminating codes or barcodes may be designed using one or more distance measures capable of evaluating a distance between codewords. In an embodiment, the distance measure may be a Hamming distance, which corresponds to the number of positions at which two codewords differ. Mathematically, if each codeword in a set of codewords has a Hamming distance of at least d from all other codewords in the set, then the code can correct up to (d−1)/2 errors, or conversely, the Hamming distance d that may accomplish decoding up to x number of errors is 2x+1. The quantity d may be referred to as the minimum distance of the code. The notation [n, k, d] may be used to characterize an error-correcting code of length n digits that encodes k information digits and has a minimum distance d. Other distance measures may be used, including a Euclidean distance measure, a sum of absolute values of differences between corresponding entries of two codewords, and a sum of squared differences between corresponding entries of two codewords, for example. In various embodiments, using such distance measures can allow a distance between codewords to be evaluated in flowspace.

In various embodiments, sample discriminating codes or barcodes may be designed to have an error-correcting code with a minimum distance of five that is capable of correcting up to two digit errors in the codewords In another embodiment, the error-correcting code may have a minimum distance of three and be capable of correcting a single digit error in the codewords. In some examples, a software algorithm or methodology that iteratively compares each codeword in a candidate group to all others in the group to construct a largest codeword set that maintains the desired minimum distance and has the desired error-correcting capability may be used to select or otherwise group codewords that comprise the error-correcting code. The codewords (or corresponding barcodes) may further be divided into subsets that, when used alone, may correct for multiple flowspace errors (e.g., two or more errors). This may allow for a set barcodes that can correct at least two flowspace errors. The barcode set may be generated using a ternary coding scheme in flowspace (e.g., in flowspace, the barcodes may be viewed as having 0, 1, or 2 incorporation(s) in a given flow).

In various embodiments, sample discriminating codes or barcodes may be designed to distinguish reads in flowspace rather than base space, which may be effective for sequencing-by-synthesis and may help avoid an excessive number of flows and thereby reduce error build-up and wasted/diminished sequencing capacity. In some instances, the Hamming distance, for example, may not be less effective in base space. For example, a single base insertion at the beginning of a sequence (e.g., AACGT vs. ACGT) would yield a Hamming distance of 3 (despite an in/del distance of only 1. Further, when translating a binary code into 4 letters by paired bits, errors automatically affect two bits simultaneously, and an error correction of 1 bit is not guaranteed to correct 1 error in base reading. Furthermore, conventional barcode designs may not appropriately address sequencing error motifs. In an embodiment, codewords may be selected for useful biological properties.

In some embodiments, sample discriminating codes or barcodes may be designed around a Hamming ternary code mapped into a particular predetermined flow ordering. For example, such a code may be a [n=13, k=10, d=3] Hamming ternary code; and such a mapping may take the first 10 "trits" (e.g., symbols of the ternary code, such as 0, 1, and 2) and assign them to some of the flows in the predetermined ordering (e.g., flows 9-18), and take three "parity check" trits and assign them to other flows (e.g., 19-21). In some embodiments, a final synchronization flow may then be a 1-mer (e.g., a 'C' at flow 22) to result in the flows terminating the codeword being zero if they are specified to be zero. Some of the codewords generated under the Hamming codes may not be permissible flowspace representations (e.g., they may be valid mathematical codewords in flowspace that do not correspond to a possible nucleic acid sequence in base space given the predetermined flow ordering). These codewords may be filtered out. In some embodiments, the codewords may be further filtered to include only codewords composed of a desired length (e.g., 9-15 bases).

In some configurations, for a multiplex sequencing application that leverages a set of 96 barcodes that can correct two errors in the flowspace string, with some accommodation for potential loss due to problematic barcodes, and a predetermined flow ordering of TACG, followed by TACG, followed by TCTG, followed by AGCA, followed by TCGA, followed by TCGA, followed by TGTA, followed by CAGC, for example, a set of barcode sequences may be generated using a ternary Hamming code of 13-digit length, with ten of the digits being treated as data and three of the digits being treated as parity checks in the codeword. This particular coding scheme yields about 140 codewords that can correct up to two errors.

In an example, barcodes may be selected having 9-11 bases in length and designed for use in oligonucleotides for multiplex sequencing on an Ion PGM™ sequencing instrument. The oligonucleotides for this example contained, in the following order, a primer site, a TCAG key sequence (e.g., key bases) for quality control and sample detection, a unique barcode sequence, a common C base at the 3' end of the barcode sequences for synchronization to ensure that flows terminating the codeword are zero if they are specified to be zero, and a GAT buffer between the barcode and the insert to minimize the influence of the variable barcode region on ligation of the adapter. This GAT buffer may be the same last three bases as the P1 adapter used for the Ion PGM™ sequencing instrument. The information in Table 1 below is organized according to the serial number of the barcodes that were generated. The second column shows the key sequence, barcode sequences, and the common C base. The third column shows the barcode sequences and the common C base. The fourth column shows the projection of the combined sequence elements into flowspace. In the table, the bases and flowspace vector elements corresponding to the barcodes are all indicated in bold. In the flowspace mapping, flows 1-8 were assigned to the key sequence (i.e., flow 1=T, flow 2=A, flow 3=C, flow 4=G, and flows 5-8 repeating flows 1-4), flows 9-18 were assigned to the data digits of the barcode (i.e., flow 9=T, flow 10=C, flow 11=T, flow 12=G, flow 13=A, flow 14=G, flow 15=C, flow 16=A, flow 17=T, flow 18=C), and flows 19-21 were assigned to the parity digits (i.e., flow 19=G, flow 20=A, and flow 21=T). Because, in this example, all the barcodes were followed immediately by a common C base, flow 22 (i.e., flow 22=C) was provided for synchronization. In an embodiment, the predetermined flow order may comprise these 22 flows and additional flows such that the flow order comprises a repeating series of 32 flows (i.e., flow 23=G, flow 24=A, flow 25=T, flow 26=G, flow 27=T, flow 28=A, flow 29=C, flow 30=A, flow 31=G, and flow 32=C. Other suitable flow orders, as described herein, may also be implemented. In other embodiments, the keys, synchronization bases, and/or buffers can be varied.

TABLE 1

Exemplary barcodes and projections into flowspace.

| Serial No. | Key + Barcode + C | Barcode + C | Flowspace Vector |
|---|---|---|---|
| 1 | TCAGTCCTCGAATC (SEQ. ID. NO. 1) | TCCTCGAATC (SEQ. ID. NO. 10) | 1010010112100010001211 |

TABLE 1-continued

Exemplary barcodes and projections into flowspace.

| Serial No. | Key + Barcode + C | Barcode + C | Flowspace Vector |
|---|---|---|---|
| 2 | TCAGCTTGCGGATC (SEQ. ID. NO. 2) | CTTGCGGATC (SEQ. ID. NO. 11) | 1010010101210010002111 |
| 4 | TCAGTCTAACGGAC (SEQ. ID. NO.. 3) | TCTAACGGAC (SEQ. ID. NO. 12) | 1010010111102010002101 |
| 5 | TCAGTTCTTAGCGC (SEQ. ID. NO. 4) | TTCTTAGCGC (SEQ. ID. NO. 13) | 1010010121201110001001 |
| 6 | TCAGTGAGCGGAAC (SEQ. ID. NO. 5) | TGAGCGGAAC (SEQ. ID. NO. 14) | 1010010110011110002201 |
| 7 | TCAGTTAAGCGGTC (SEQ. ID. NO. 6) | TTAAGCGGTC (SEQ. ID. NO. 15) | 1010010120002110002011 |
| 9 | TCAGCTGACCGAAC (SEQ. ID. NO. 7) | CTGACCGAAC (SEQ. ID. NO. 16) | 1010010101111020001201 |
| 11 | TCAGTCTAGAGGTC (SEQ. ID. NO. 8) | TCTAGAGGTC (SEQ. ID. NO. 17) | 1010010111101101002011 |
| 12 | TCAGAAGAGGATTC (SEQ. ID. NO. 9) | AAGAGGATTC (SEQ. ID. NO. 18) | 1010010100002101002121 |

In various embodiments, sample discriminating codes or barcodes may be designed around an [n=11, k=6, d=5] ternary Golay code using values 0, 1, and 2. Such a code has 729 (i.e., $3^6$) distinct codewords of length 11 with a distance of 5 between the codewords to correct 2 errors. The codewords may be generated linearly or cyclically or using any suitable methods, such as, for example, through a generator matrix or a generator polynomial. In other embodiments, variance in the key bases (or flows) used for the barcode (or flowspace codeword) and variance in a terminating base (e.g., terminating "C" base and/or and corresponding terminating "1" flow) can generate additional barcodes for use in multiplexing reactions. For instance, where use of common key bases (or flows) and a terminating static base limits the number of eligible barcode sequences for use in multiplexing (e.g., up to 96 barcode sequences, or up to 384 barcode sequences), variance in these properties can generate a greater number of barcode sequences for use in multiplexing (e.g., at least 1000 barcode sequences).

Figure 7:
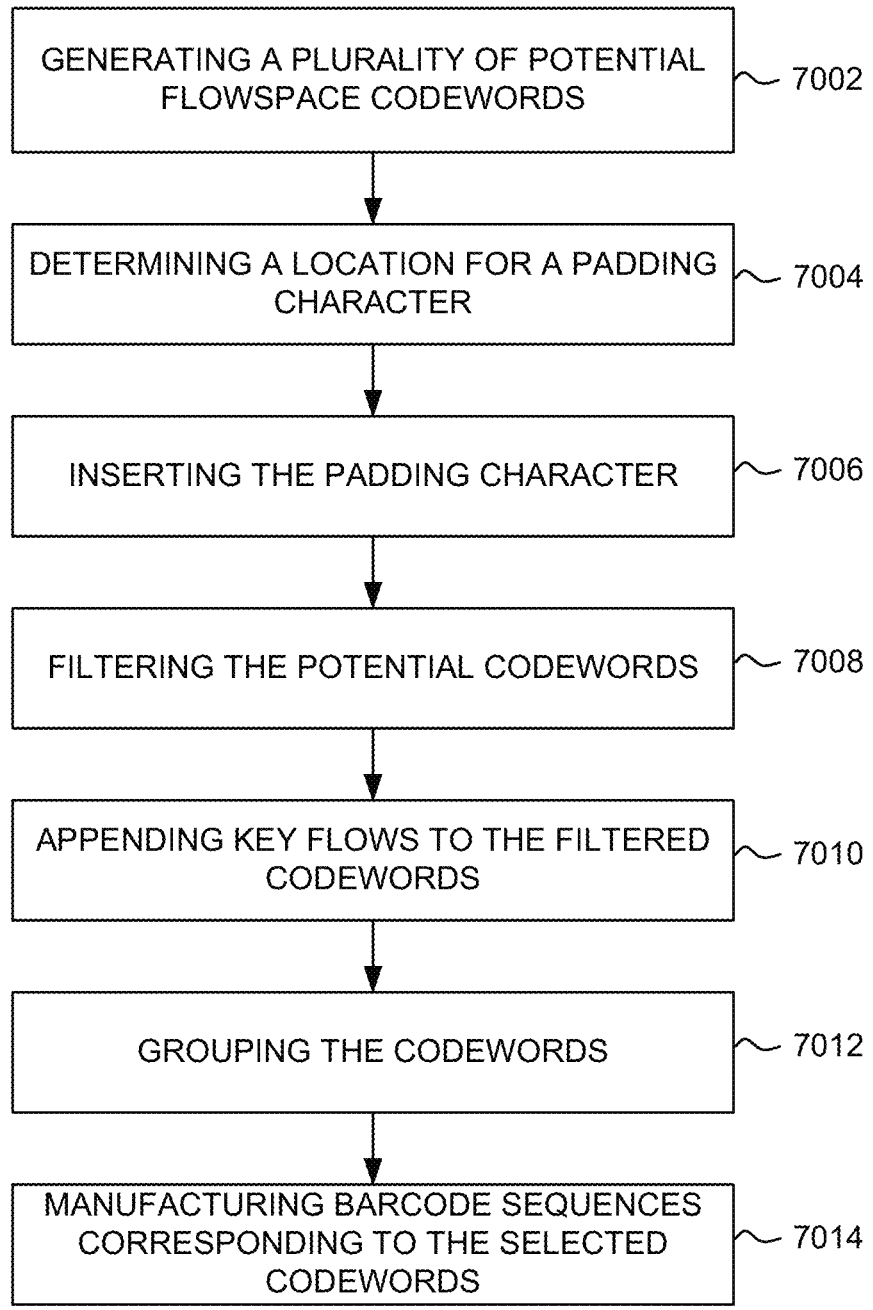
FIG. 7 illustrates an exemplary method for designing barcode sequences corresponding to flowspace codewords.

FIG. 7 illustrates an exemplary method for designing barcode sequences corresponding to flowspace codewords. At step 7002, a plurality of potential flowspace codewords may be generated. For example, a generator function may generate a set of potential flowspace codewords using a ternary [n=13,k=10,d=3] Hamming code of 13-digit length, with ten of the digits being treated as data and three of the digits being treated as parity checks in the codeword. The number of generated potential codewords may comprise n^k, or in this example 3^10. The generated flowspace codewords may comprise an ordered series of characters, such as alpha-numeric characters or other symbols. Other configurations of Hamming codes or Golay codes may similarly be implemented. The codewords may be generated linearly or cyclically or using any suitable methods, such as, for example, through a generator matrix or a generator polynomial.

At step 7004, a location may be determined for a padding character within the potential flowspace codewords. For example, in some configurations, a base, such as a padding base, may be appended to the end of barcodes in order to aid in sequencing. In the flowspace, according to a predetermined flow order, the padding base may correspond to a padding flow. For instance, padding base may comprise a "C" and, according to the predetermined flow order, the corresponding padding flow (or character) may comprise a "1." In these configurations, the flowspace codewords may be appended with a terminating "1" and similarly the corresponding barcode sequences may be appended with a terminating C. For example, where the generated flowspace codewords comprise 13 characters, after addition of the padding character, the codeword may comprise 14 characters. In an embodiment, the predetermined flow ordering may comprise an ordering based on a cyclical, repeating pattern of flow ordering, based on a random flow ordering, or based on an ordering comprising in whole or in part a phase-protecting flow ordering, or some combination thereof.

In some embodiments, the padding character may be moved such that it is not at the terminating flow of a codeword (and the corresponding padding base is not the terminating base of a barcode sequence). This flexibility in relocating the padding character/base will give rise to a number of potential options for locations such that design benefits may be achieved. For example, insertion of the padding character into a 13 character flowspace codeword at a selected location may increase the number of codewords that map to a valid base space sequence according to the predetermined flow order. Based on the known dNTP reagent flowed and the incorporation status (e.g., 0, 1, 2, or the like) of the reagent, corresponding base space sequences may be determined for the flowspace codewords according to the predetermined flow order. While the translated sequences may differ in base length, they may nonetheless be synchronized in the flow space based on the corresponding synchronized flowspace codewords.

In an embodiment, some codewords may fail to translate to a valid base space sequence according to the predetermined flow order. In an example, given the flow order "A" "G" "A," a flowspace string (or vector) of 101 will not translate to a valid base space. Here, the second incorporation (e.g., the second occurrence of 1 of 101) would not translate to valid base sequences. For example, where two "A's" were present in the barcode without an intervening base, the first flow of "A" would exhibit a 2-mer (e.g., would render a flowspace value of 2) thus rendering the second incorporation impossible. Other methods to determine invalid base space translations may be implemented.

In an embodiment, insertion of the padding character at various locations in the codewords may provide an adjustment such that a plurality of codewords that previously failed to map to a valid base space sequence successfully map to a valid base space sequence after insertion. In some examples, the location that results in the highest number of codewords that correspond to valid base space sequences may be selected. Here, the selected location for insertion of the padding base may be consistent for the generated codewords in order to preserve the distance properties of the codewords (e.g., maintain the distance properties used to generate the codewords).

In an embodiment, determining a location for the padding character within the flowspace codewords may comprise iterating over a plurality of locations for the padding character within the codewords such that, based on inserting the padding character at the iterated location into the codewords, a number of codewords that correspond to valid base space sequences according to the predetermined flow order may be calculated for each location. For example, given a codeword having a length of 13, 14 possible locations exist for the padding character (i.e., prior to the first character, between the first character and the second character, and so on). Here, an algorithm may be designed such that the padding character is inserted iteratively through these 14 possible locations and, for each iteration, a number of codewords after insertion of the padding flow at the iterated location that map to valid base space sequences may be calculated. For instance, the algorithm may determine whether the codewords, after insertion at the iterated location, map to a valid base space sequence according to the predetermined flow order. The number of these codeword that map to valid base space sequences may then be calculated for each iterated location.

In an embodiment, calculating the number of flow space codewords that map to a valid base space sequence according to the predetermined flow order for a given iterated location may further comprise determining the base space sequences corresponding to the flowspace codewords that map to valid base space sequences after inserting the padding character at the iterated location. In some embodiments, the calculated number of codewords may comprise the number of determined base space sequences. In other embodiments, the determined base space sequences may be further filtered. For example, the determined base space sequences may be filtered out according to one or more of a sequence length criteria and a percentage of nucleotide content (e.g., GC content) criteria, and other suitable criteria. For example, a sequence length criteria may comprise 9-11 bases or 9-14 bases, and determined base space sequences greater than the criteria may be filtered out. Other suitable length ranges may also be implemented.

In another example, barcode sequences may be designed or selected to avoid certain nucleotide sequences known to cause sequencing read errors or result in sequencing bias. This can enhance PCR and/or sequencing performance. In some embodiments, because the GC (guanine/cytosine) content of a sequence can affect sequencing quality, a filtering criteria may comprise a GC content within the range of 40-60%. The AT content may also be similarly treated. In an example, determined base space sequences that do not meet the GC and/or AT content criteria may be filtered out.

In an embodiment, the calculated number of flowspace codewords that map to a valid base space sequence according to the predetermined flow order for a given iterated location may comprise the number of determined base space sequences after filtering.

In an example, after iterating over the possible locations for the padding character, for instance over a 13 character flowspace, the location that corresponds to the highest calculated number may be selected. This selected location will generate a larger number of flowspace codewords that map to a valid base space sequence, and thus a larger number of corresponding barcode sequences (e.g., available for multiplexing).

The following example is presented to illustrate the above principle. In this example, the selected location may comprise flow 5 of the flowspace codewords (e.g., selected based on this location corresponding to the highest calculated number). The example will illustrate how the flexibility of relocating the padding character from the terminating flow to a selected location is used to adjust a codeword that previously did not translate to a valid base space such that, after insertion of the padding based at the selected location, the codeword successfully maps to a valid base space sequence. Using a sample generated flow space codeword of "20012220010121" and a sample flow order of "T C T G A G C A T C G A T C" (SEQ. I.D. NO. 19), the flowspace code word may include a padding terminating character of "1." According to the sample flow order, the sample flowspace codeword does not map to a valid base space sequence while the padding character is located at terminating flow at least because two successive incorporations occur with no base incorporation in between. For example, when considering a hypothetical synchronized flow, the underlined flowspace symbols of the codeword 2001222_00_10121 would correspond to the underlined flows of the sample flow order T C T G A G CATC G A T C (SEQ. I.D. NO. 19). Here, the leading "2" represents a 2-mer incorporation when the leading "C" is flowed. The following "00" represents two 0-mers when the subsequent "A" and "T" are flowed. However, the subsequent "1" in the flowspace codeword, representing a 1-mer, could not be generated based on the corresponding "C" flow of the sample flow order. This is at least because, if such a complementary base were present, the leading "2" that incorporated as a result of the leading "C" flow would have incorporated as a "3" or 3-mer. In this example, relocation of the padding character from the 14$^{th}$ flow to the 5$^{th}$ flow will result in a valid base space sequence according to the sample flow order. This relocation results in the codeword "2001_1_222001012." The adjusted flowspace codeword would then map to a valid base space translation according to the same sample flow order. One of ordinary skill in the art would appreciate, based on the teachings of the present disclosure, that other possible relocation positions may similarly be implemented that also result in a valid base space translation.

Another example also illustrates how the flexibility of relocating the padding character from the terminating flow to a selected location (e.g., also the 5$^{th}$ flow as above) is used to adjust a codeword that previously did not translate to a valid base space such that, after insertion of the padding based at the selected location, the codeword successfully maps to a valid base space sequence. Using a sample generated flowspace codeword of "00000210220211" and a sample flow order of "T C T G A G C A T C G A T C" (SEQ. I.D. NO. 19), the flowspace codeword may also comprise a padding terminating flow of "1." In this example, a series of key flows also may be utilized. For example, a series of key bases may precede a barcode, for tracking barcodes and/or attached targets. The key flows in the sample ordering (e.g., the series of flows that directly precede the sample ordering) may comprise "T A C G" followed by a repeated flow order of "T A C G." According to the sample flow order and the key flows, the sample flowspace codeword does not map to a valid base space sequence while the padding character is located at the terminating flow at least because too many flows results in a 0-mer after the key flows. For example, for a hypothetical synchronized flow, the underlined flowspace symbols of the codeword 00000210220211 would correspond to the underlined flows of the sample flow order TCTGA G C A T C G A T C (SEQ. I.D. NO. 19). Here, the last key flow comprises a "G." In the highlighted series of flows, all 3 other possible dNTPs other than G are flowed in the series of 5 flows, and thus in order for the codeword to map to a valid flowspace, at least one of these flows would have to result in an incorporation. In this example, relocation of the padding character from the $14^{th}$ flow to the $5^{th}$ flow will result in a valid base space sequence according to the sample flow order. This relocation results in the codeword "00000121022021." The adjusted flowspace codeword would then map to a valid base space translation according to the same sample flow order. One of ordinary skill in the art would appreciate, based on the teachings of the present disclosure, that other possible relocation positions may similarly be implemented that also result in a valid base space translation.

In this embodiment, the flowspace codewords maintain synchronization after insertion of the padding character. For instance, the flowspace codewords after insertion will comprise a length X plus the inserted character (e.g., X+1. Thus, the codewords may still be synchronized relative to flow length and the predetermined flow order.

At step 7006, the padding character may be inserted into the flowspace codewords at the determined location. For example, a location may be selected for the padding character based on, for instance, calculated numbers for the possible locations as described herein. The flowspace codewords may then be adjusted by inserting the padding character at the selected location into the codewords, as described herein. In an embodiment, the insertion may be performed on the set of generated codewords such that the error-tolerant properties of the codewords are maintained (e.g., minimum distance properties are maintained).

At step 7008, the potential flowspace codewords may be filtered. For example, flowspace codewords that do not map to a valid base space according to the predetermined flow order may be filtered out. The filtering of potential flowspace codewords may take place after insertion of a padding base at a selected location into the codewords. Here, some codewords that did not previously map to valid base space sequences may be kept (e.g., not filtered out) based on insertion of the padding base at the selected location. For instance, examples of how relocating a padding base from a terminating flow to a selected flow (e.g., flow 5) results in a codeword that maps to a valid base space sequences are further described herein.

In some embodiments, the flowspace codewords also may be filtered according to base space sequence length. For example, potential flowspace codewords that comprise base space translations according to the predetermined flow ordering greater than a threshold length may be filtered out. For example, a sequence length criteria may be 9-11 bases or 9-14 bases, and flowspace codewords that correspond to base space sequences greater than the criteria may be filtered out. Other suitable length ranges may also be implemented.

In some embodiments, potential flowspace codewords may be filtered according to minimum distance. For example, sorting algorithms may be implemented that select a subset of potential flowspace codewords with predetermined minimum distances. In an example, groups of codewords may be selected such that they achieve a first minimum distance from each other and a second minimum distance from other codewords in other groups. Potential codewords that are not selected by such sorting algorithms may similarly be filtered out.

In some embodiments, potential codewords may be filtered out according to percentage of nucleotide content (e.g., GC content). For example, the barcode sequences may be designed or selected to avoid certain nucleotide sequences known to cause sequencing read errors or result in sequencing bias. This can enhance PCR and/or sequencing performance. In some embodiments, because the GC (guanine/cytosine) content of a sequence can affect sequencing quality, a filtering criteria may comprise a GC content within the range of 40-60%. The AT content may also be similarly treated. In an example, potential codewords that translate to base space sequences that do not meet the GC and/or AT content criteria may be filtered out.

In some embodiments, potential codewords may be filtered out according to secondary structure or performance in experiments. For instance, barcode sequences that are self-complementary or complementary with a primer sequence that is coupled to the barcode may not perform well in experiments. Accordingly, potential codewords that translate to base space sequences that are self-complementary or complementary with a primer sequence that is coupled to the barcode may be filtered out.

At step 7010, key flows may be appended to the filtered codewords. For example, key flows may be used in tracking barcodes, or corresponding nucleic acid fragments (e.g., target nucleic acids). Key flows may correspond to key bases according to the predetermined flow ordering. In some embodiments static key bases (e.g., "T," "C," "A," "G,") may be used and appended to barcode sequences. In this example, the corresponding flowspace string according to the predetermined flow ordering may similarly comprise static key flows (e.g., 10100101) which can be appended to the flowspace codewords.

In some embodiments, variable key flows (or bases) may be implemented to further distance flowspace codewords from one another. For instance, two different possible sets of key bases may be used that vary based on a repeating terminating base (e.g., "T," "C," "A," "G," and "T," "C," "A," "G," "G"). In this example, variance in the corresponding flowspace according to the predetermined flow order may comprise either a "1" or a "2" in the last key flow (e.g., 10100101 and 10100102). In an embodiment, the two different key flows may be appended to flowspace codewords to further distance the codewords from one another.

In some embodiments, the set of filtered codewords may be duplicated, where a first set of the codewords is appended with a first of the key flows and the duplicate set of codewords is appended with the second of the key flows. Here, two versions of the same codeword may differ by the key flows appended to the codeword (e.g., by the "1" or "2" for the terminating key flow). The variance in key flows may effectively increase the minimum distance between the codewords by at least one.

In other embodiments, other variable key flows (or bases) may similarly be implemented. For instance, the terminating flows may comprise a "1," "2," or "3," such that three different key flows may be generated and appended to the codewords. In other embodiments, other differences in key flows may similarly be implemented to increase the distance between codewords.

At step 7012, the filtered codewords may be selected and grouped. For example, the codewords may be grouped according to minimum distances. In an embodiment, sorting algorithms may be implemented that select a subset of codewords with predetermined minimum distances. In an example, groups of codewords may be selected such that they achieve a first minimum distance from each other and a second minimum distance from other codewords in other groups. In some embodiments, the minimum distance used by the sorting algorithm may include the effective increase in minimum distance caused by appending variable key flows to the codewords. In an embodiment, the first minimum distance may be greater than the second minimum distance. For instance, the first minimum distance may comprise 6 while the second minimum distance may comprise 4. In some embodiments, one or more of the groups of codewords may comprise a universal group such that the codewords in the universal group comprise the first minimum distance from all the other codewords (e.g., within the group and every other group. Other suitable minimum distance values may be implemented.

In an embodiment, individual groups of codewords may comprise first error-tolerant codes and the selected barcodes in total (e.g., the groups in combination) may comprise a second error tolerant code. For instance, the first error-tolerant code may be defined by the minimum distance between codewords within the same group and the second error-tolerant code may be defined by the minimum distance between codewords from different groups. Based on the different minimum distances, the first error tolerant codes may be able to resolve and/or correct a greater number of errors in sequencing than the second error-tolerant code.

In an embodiment, after filtering and sorting, the grouped flowspace codewords may include at least 500 codewords, 1000 codewords, 3000 codewords, 5000 codewords, 7000 codewords, or 9000 codewords. A representative list of barcodes corresponding to these grouped codewords in accordance with the present disclosure, for example, using the techniques described above with reference to FIG. 7, can be seen at Table 2 below and in Appendix A of U.S. Pat. Appl. No. 62/161,309, filed May 14, 2016, to which this application claims priority and which is incorporated by reference herein in its entirety.

At step 7014, barcodes corresponding to the grouped flowspace codewords may be manufactured or caused to be manufactured. For instance, the barcodes corresponding to the grouped flowspace codewords according to the predetermined flow ordering may be manufactured in accordance with the details presented herein. In some example, manufacturing may include causing said barcodes to be manufactured. In an embodiment, the grouped and manufactured barcodes may include at least 500 barcodes, 1000 barcodes, 3000 barcodes, 5000 barcodes, 7000 barcodes, or 9000 barcodes.

In an embodiment, barcodes corresponding to grouped codewords may be organized by plate. For example, codewords selected for a group, as described herein, may correspond to a group of barcodes. This group of barcodes may be organized by plate (e.g., structure storing the grouped barcodes). As such, barcodes of a particular plate may comprise the error-tolerant properties (e.g., minimum distance properties) of grouped codewords corresponding to those barcodes and barcodes from plate to plate may comprise the error-tolerant properties (e.g., minimum distance properties) of non-grouped codewords corresponding to those barcodes.

In a various exemplary embodiments, when manufacturing the barcodes, a plurality of barcode adaptors may be appended to the barcode sequences. However, barcodes corresponding to codewords that have been adjusted (e.g., where a terminating static or padding flow, and the corresponding base, has been relocated) no longer comprise a static terminating output signal (e.g., in flowspace) when being sequenced according to the predetermined flow order. Here, the terminating output signal (e.g., in flowspace) may be predicted based on the predetermined flow order and the flowspace codeword. In an embodiment, the barcodes may be split into two categories in which, for example, the first category comprises barcodes that conclude with a positive incorporation signal according to the predetermined flow order (e.g., a "1" or "2" in flowspace) and the second category comprises barcodes that do not (e.g., a "0" in flowspace). In some embodiments, the barcodes in the first category may use any suitable adaptor (e.g., a universal adaptor). However, barcodes in the second category may use adaptors that start with a particular base (e.g., G) due to the lack of an incorporation signal in the terminating flow in order to mitigate against potential sequencing errors. The particular base may comprise a predetermined base according to the predetermined flow order. For instance, the particular base may be predetermined such that an expected dNTP flow based according to the predetermined flow order results in an incorporation (e.g., generates an incorporation signal).

In an embodiment, the barcode manufacturing may comprise manufacturing of the forward barcode, forward primer (P1a), reverse barcode, and reverse primer (P1b). In an embodiment, in an initial step these oligonucleotides may be purified, where all of the oligonucleotides are normalized to 100-400 μM in a TE or low TE buffer. In an embodiment, the oligonucleotides that are non-ligating (e.g., the reverse barcode and P1b) may be purified using High Performance Liquid Chromatography (HPLC) while the oligonucleotides that are ligating (e.g., the forward barcode and P1a) may be purified using a desalting technique. Those having ordinary skill in the art are familiar with various desalting techniques that can be used in barcode manufacturing.

For instance, use of HPLC for the reverse barcode and P1b may help mitigate against sequencing error. Oligonucleotides are synthesized from 3' to 5', and thus failed syntheses from reverse barcode and P1b are potentially truncated at the 5' end. A lack of HPLC treatment for these strands may increase adapter dimer (e.g., from substantially 0% to substantially 5-15%). In addition, the forward barcode and P1a are directly ligated to the amplicon and any cross-contamination may lead to base miscalling. In addition, with a large number of sequences, HPLC may be both cost-prohibitive (or otherwise cost inefficient) and prone to cross-contamination. Desalting these strands rather than performing HPLC is less expensive and does not require the strands to be used on common lab equipment (i.e., HPLC instrument) thus eliminating a source of cross contamination. Further, during nick translation, the reverse barcode and P1b are overwritten by DNA polymerase using the forward barcode and P1a as a template, thus removing any contamination originating from HPLC contamination of P1b and reverse barcode sequences. This further reduces contamination risk for the strands on which HPLC is performed.

In an embodiment, after purification, equal volumes of forward and reverse barcode oligonucleotides and P1a and P1b oligonucleotides may be combined and annealed in separate tubes using certain annealing conditions. For example, the annealing conditions may comprise: denaturing at 95° C. for 5 minutes; performing 64 cycles starting at 89° C. for 2 minutes with a 1° C. decrease every 2 minutes; and holding at 4° C. for 1 hour and up to overnight (e.g., between 6 and 12 hours).

After annealing, equal volumes of annealed barcode adaptor and P1 adaptor may be combined. The sample may be diluted 5-fold with a low TE buffer. And 2 µL of diluted mixture/AmpliSeq reaction may be added. Other variations of barcode manufacturing may similarly be implemented.

In an embodiment, the step of manufacturing the barcodes may comprise synthesizing the polynucleotide. A polynucleotide containing the barcode sequence may be made using any conventional polynucleotide synthesis technique known in the art.

According to various exemplary embodiments, the manufactured barcodes may be combined to form a kit of barcodes for use for sequencing. For example, the grouped barcodes may be apportioned to one or more plates, or other platforms useful for sequencing of nucleic acids, including multiplex sequencing. For instance, codewords corresponding to barcodes within a particular plate may have a first minimum distance from other codewords corresponding to barcodes within the particular plate and a second minimum distance from codewords corresponding to barcodes of other plates. In some embodiments, a plate of barcodes may comprise a flex plate such that codewords corresponding to barcodes within in the flex plate comprise the first minimum distance from codewords corresponding to all the other barcodes of the kit. Here, the barcodes of the flex plate may be used as substitute barcodes for all other plates given the minimum distance properties of the flowspace codewords corresponding to the barcodes. Kits of barcodes may be customized based on desired applications by selecting some of the valid barcodes, or may include a comprehensive set of barcodes.

The sequencing kit may further comprise a polymerase enzyme. The sequencing kit may further comprise multiple containers for holding the different polynucleotides, and each different polynucleotide may be held in a different container. The polynucleotides may be oligonucleotides of 5-40 bases in length. The sequencing kit may further comprise multiple different kinds of nucleotide monomers. The sequencing kit may further comprise a ligase enzyme.

In some embodiments, the sequencing kit may comprise multiple different polynucleotides (which may be contained in vials, for example), each different polynucleotide comprising a different barcode sequence as described herein. The polynucleotides may be oligonucleotides having 5-40 bases. The polynucleotides may be the barcode sequences themselves, or they may further include other elements, such as primer sites, adaptors, ligating sites, linkers, etc. The sequencing kit may also include a set of precursor nucleotide monomers for carrying out sequencing-by-synthesis operations, for example, and/or various other reagents involved in a workflow for preparing and/or sequencing a sample.

In an embodiment, barcodes, or groupings of barcodes, may be used to perform multiplexing. For instance, unique barcodes may be attached to a plurality of target nucleic acids such that the target nucleic acids may be identified after sequencing by the unique barcode sequences (or flowspace representations).

Figure 8:
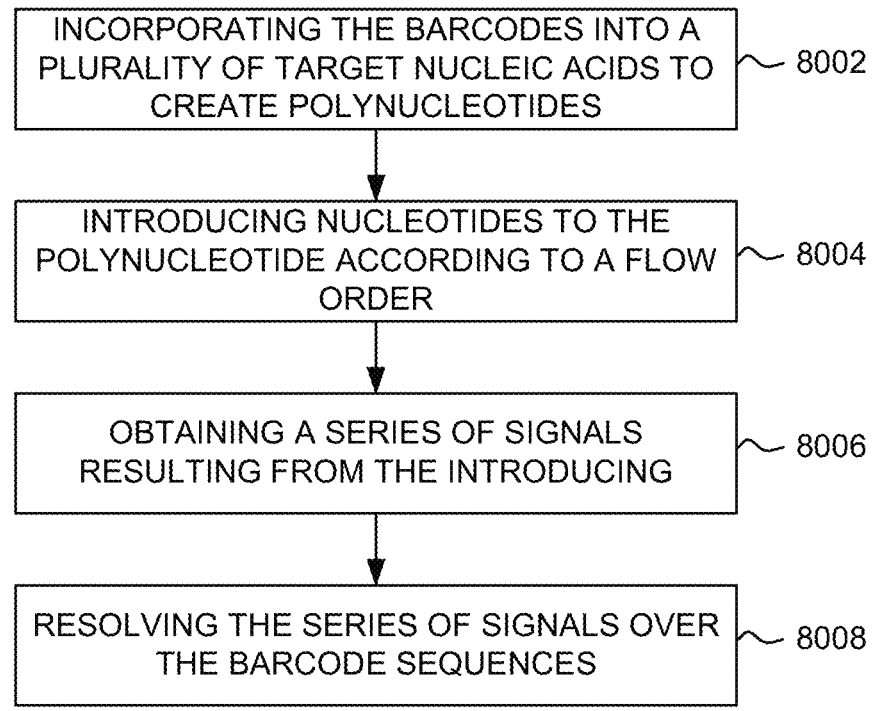
FIG. 8 illustrates an exemplary method for sequencing polynucleotide samples with a barcode sequences.

FIG. 8 illustrates a method for sequencing polynucleotide samples with barcode sequences according to exemplary embodiments of the present disclosure. For example plurality of barcodes that correspond to flowspace codewords according to a predetermined flow order in accordance with exemplary embodiments described herein.

At step 8002, the plurality of barcodes may be incorporated into a plurality of target nucleic acids to create polynucleotides. For example, the barcodes may be attached to the target nucleic acids by any conventional means such that signals obtained over the barcodes during sequencing may identify the particular target nucleic acid attached to the barcode.

In an embodiment, multiple different target nucleic acids for multiplex sequencing by the predetermined flow of nucleotides may be provided, with each different target nucleic acid being attached to a different provided barcode sequence that corresponds to a different flowspace string, and with each different flowspace string being a different codeword of the error-tolerant or error-correcting code. In an embodiment, the barcodes that are utilized may be at least 500 barcodes, 1000 barcodes, 3000 barcodes, 5000 barcodes, 7000 barcodes, or 9000 barcodes. Similarly, in an embodiment, the different target nucleic acids may be at least 500, 1000, 3000, 5000, 7000, or 9000.

At step 8004, a series of nucleotides may be introduced to the polynucleotides according to the predetermined flow order. For instance, flows of dNTP reagents may be flowed according to the predetermined flow order such that the polynucleotides are exposed to the flows and incorporation events may occur.

At step 8006, a series of signals resulting from introducing the series of nucleotides may be obtained. For example, hydrogen ions released by the incorporation of nucleotides into the polynucleotides may be detected, wherein the amplitude of the signals may be related to the amount of hydrogen ions detected. In another example, inorganic pyrophosphate released by the incorporation of nucleotides into the polynucleotide may be detected, wherein the amplitude of the signals is related to the amount of inorganic pyrophosphate detected.

At step 8008, a series of signals over the barcode sequences may be resolved to render flowspace strings such that the rendered flowspace strings are matched to the codewords, wherein at least one rendered flowspace string is matched to at least one codeword in the presence of one or more errors. In an embodiment, the series of signals may comprise a flowspace vector or string comprising of symbols (e.g., 0, 1, 2, and the like) that represent a number of incorporations for a given flow (e.g., 0-mer, 1-mer, 2-mer, and the like).

In an embodiment, any suitable decoding algorithms and/or software tools may be used for decoding the flowspace strings from the barcode sequences to correct and/or detect errors. For example, the decoding can be performed using an exhaustion algorithm in which a codeword with an error is compared to all other members of the code and decoded as the closest matching codeword. If the codeword with the error is equally close to two codewords or is further than half the minimum distance from any codeword, then the algorithm may indicate that an error is detected without making any corrections. In another example, the decoding may involve performing the coding operation in reverse. In another example, the decoding algorithm may use linear algebra techniques to decode the codeword.

In an embodiment, once the at least one codeword with the error is matched to a codeword of the error-tolerant code or error-correcting code, signals obtained over one of the target nucleic acid sequences associated with the barcode corresponding to the matched flowspace codeword may be identified. For example, a rendered flowspace string, and corresponding base space sequence, may be identified for the target nucleic acid based on the matched codeword.

In some embodiments, the scale of multiplexing that is enabled by the large number of provided barcodes may facilitate certain sequencing applications. For example, genotyping by sequencing, clone verification, and other test synthesis verification (e.g., to verify a synthesized sequence is correct) may be performed more efficiently with a large number of barcodes that enable a high degree of multiplexing. In some embodiments, there is also provided a non-transitory machine-readable storage medium comprising instructions which, when executed by a processor, cause the processor to perform such methods and variants thereof as detailed herein. There is also provided a system, including: a machine-readable memory; and a processor configured to execute machine-readable instructions, which, when executed by the processor, cause the system to perform such methods and variants thereof as detailed herein.

According to an exemplary embodiment, there is provided a pool of different polynucleotide strands, each different polynucleotide strand comprising a different barcode sequence; wherein the flowspace projection of each different barcode sequence according to a predetermined flow ordering gives different flowspace strings that are codewords of an error-tolerant code, as detailed herein. FIG. 9 illustrates a pool of seven different polynucleotide strands, each associated with a unique barcode sequence. Various embodiments include larger numbers of barcode sequences and polynucleotide strands, with the seven described polynucleotides being representative examples. Each polynucleotide strand may have a primer site, a standard key sequence, and a unique barcode sequence. Each polynucleotide strand also may have a different target sequence. Such a pool of polynucleotide strands may be subject to multiplex sequencing and the barcodes may help identify the source of the sequence data derived from a multiplex sample.

According to an exemplary embodiment, there is provided a sample identification kit, comprising: a plurality of sample discriminating codes, wherein: a) each sample discriminating code comprises a sequence of individual subunits; b) the sequence of subunits of each sample discriminating code is distinguishable from the sequence of individual subunits of each other member of the plurality of sample discriminating codes; and c) each sample discriminating code is tolerant to one or more errors so as to be discretely resolvable with respect to other sample discriminating codes.

According to an exemplary embodiment, there is provided a sample identification kit, comprising: a plurality of sample discriminating codes, wherein: a) each sample discriminating code comprises a sequence of individual subunits; b) a detectable signal is associated with each subunit or with pairs or sets of subunits such that each sample discriminating code is associated with a sequence of detectable signals; c) each sequence of detectable signals is distinguishable from the sequence of detectable signals of each other member of the plurality of sample discriminating codes; and d) the sequence of detectable signals of each sample discriminating code is tolerant to at least one error so as to be discretely resolvable with respect to other sample discriminating codes.

Figure 10A:
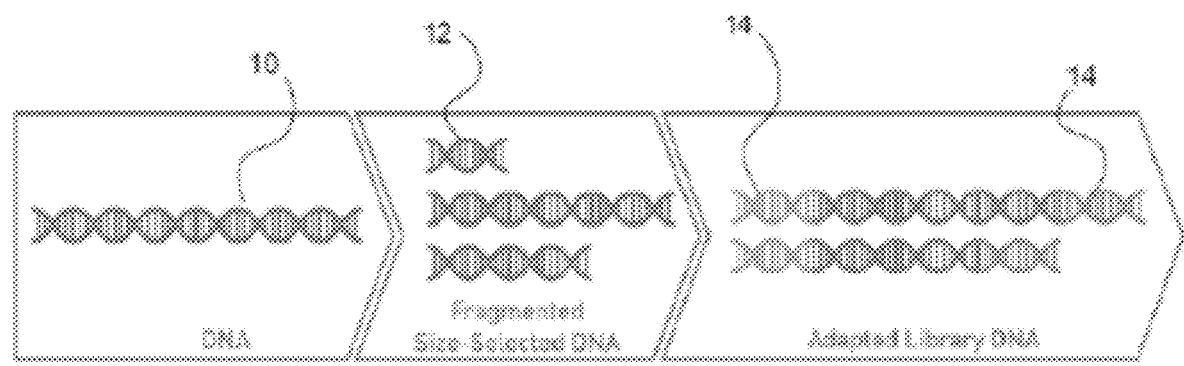
FIGS. 10A-10C illustrate an exemplary workflow for preparing a multiplex sample.
Figure 10B:
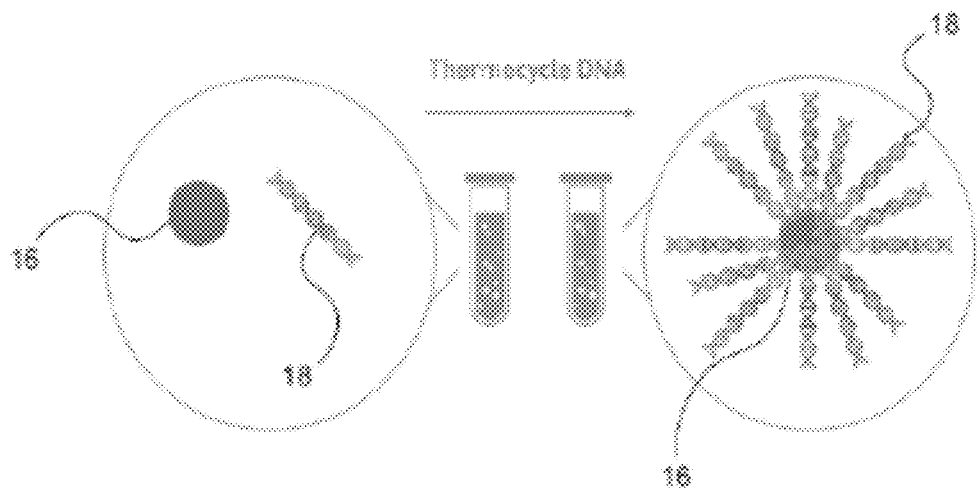
Figure 10C:
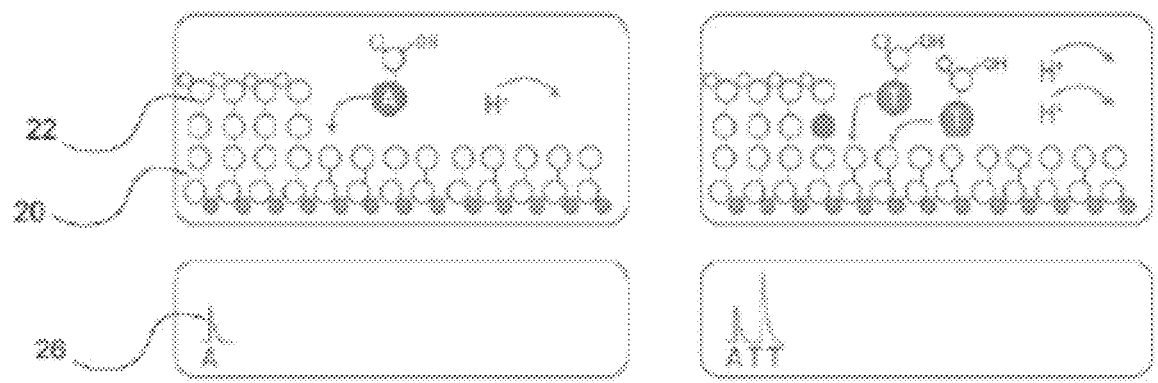

FIGS. 10A-10C illustrate an exemplary workflow for preparing a multiplex sample. FIG. 10A shows an exemplary construction of a genomic DNA fragment library. A bacterial genomic DNA 10 may be fragmented into many DNA fragments 12 using any suitable technique, such as sonication, mechanical shearing, or enzymatic digestion, for example. Platform-specific adaptors 14 may then be ligated onto the ends of the fragments 12. Referring to FIG. 10B, each fragment sample 18 may then be isolated and combined with a bead 16. To allow for identification of the fragment 18, a barcode sequence (not shown in the figure) may be ligated to the fragment 18. The fragment 18 may then be clonally amplified onto the bead 16, resulting in many clonal copies of the fragment 18 on the bead 16. This process may repeated for each different fragment 12 of the library, resulting in many beads, each having the product of a single library fragment 12 amplified many times. Referring to FIG. 10C, the beads 16 may then be loaded onto a reaction chamber array (e.g., microwell array). FIG. 10C shows a partial view of a DNA fragment inside a reaction chamber as it is undergoing sequencing reactions. A template strand 20 may be paired with a growing complementary strand 22. In the left panel, an A nucleotide is added to the reaction chamber, resulting in a single-base incorporation event, which generates a single hydrogen ion. In the right panel, a T nucleotide is added to the reaction chamber, resulting in a two-base incorporation event, which generates two hydrogen ions. The signal produced by the hydrogen ions are shown as peaks 26 in the ionograms. In various embodiments, a sequencing kit may contain one or more of the materials needed for the above sample preparation and sequencing workflow, including reagents for performing DNA fragmentation, adaptors, primers, ligase enzymes, beads or other solid support, polymerase enzymes, or precursor nucleotide monomers for the incorporation reactions.

According to an exemplary embodiment, there is provided a system, comprising a plurality of identifiable nucleic acid barcodes. The nucleic acid barcodes may be attached to, or associated with, target nucleic acid fragments to form barcoded target fragments (e.g., polynucleotides). A library of barcoded target fragments may include a plurality of a first barcode attached to target fragments from a first source. Alternatively, a library of barcoded target fragments may include different identifiable barcodes attached to target fragments from different sources to make a multiplex library. For example, a multiplex library may include a mixture of a plurality of a first barcode attached to target fragments from a first source, and a plurality of a second barcode attached to target fragments from a second source. In the multiplex library, the first and second barcodes may be used to identify the source of the first and second target fragments, respectively. Any number of different barcodes may be attached to target fragments from any number of different sources. In a library of barcoded target fragments, the barcode portion may be used to identify: a single target fragment; a single source of the target fragments; a group of target fragments; target fragments from a single source; target fragments from different sources; target fragments from a user-defined group; or any other grouping that may require or benefit from identification. The sequence of the barcoded portion of a barcoded target fragment may be separately read from the target fragment, or read as part of a larger read spanning the barcode and the target fragment. In a sequencing experiment, the nucleic acid barcode may be sequenced with the target fragment and then parsed algorithmically during processing of the sequencing data. In various embodiments, a nucleic acid barcode may comprise a synthetic or natural nucleic acid sequence, DNA, RNA, or other nucleic acids and/or derivatives. For example, a nucleic acid barcode may include nucleotide bases adenine, guanine, cytosine, thymine, uracil, inosine, or analogs thereof. Such barcodes may serve to identify a polynucleotide strand and/or distinguish it from other polynucleotide strands (e.g., those containing a different target sequence of interest), and may be used for various purposes, such as tracking, sorting, and/or identifying the samples, for example. Because different barcodes can be associated with different polynucleotide strands, such barcodes may be useful in multiplexed sequencing of different samples.

Multiplex Libraries

In various embodiments, there are provided sample discriminating codes or barcodes (e.g., nucleic acid barcodes) that may be attached to, or associated with, targets (e.g., nucleic acid fragments) to generate barcoded libraries (e.g., barcoded nucleic acid libraries). Such libraries may be prepared using one or more suitable nucleic acid or biomolecule manipulation procedures, including: fragmenting; size-selecting; end-repairing; tailing; adaptor-joining; nick translation; and purification, for example. In various embodiments, nucleic acid barcodes may be attached to, or associated with, fragments of a target nucleic acid sample using one or more suitable procedure, including ligation, cohesive-end hybridization, nick-translation, primer extension, or amplification, for example. In some embodiments, nucleic acid barcodes may be attached to a target nucleic acid using amplification primers having a particular barcode sequence.

In various embodiments, a target nucleic acid or biomolecule (e.g., proteins, polysaccharides, and nucleic acids, and their polymer subunits, etc.) sample may be isolated from any suitable source, such as solid tissue, tissue, cells, yeast, bacteria, or similar sources, for example. Any suitable methods for isolating samples from such sources may be used. For example, solid tissue or tissue may be weighed, cut, mashed, homogenized, and the sample may be isolated from homogenized samples. An isolated nucleic acid sample may be chromatin, which may be cross-linked with proteins that bind DNA, in a procedure known as ChIP (chromatin immunoprecipitation). In some embodiments, samples may be fragmented using any suitable procedure, including cleaving with an enzyme or chemical, or by shearing. Enzyme cleavage may include any type of restriction endonuclease, endonuclease, or transposase-mediated cleavage.

Fragment Libraries

In various embodiments, there are provided fragment libraries, which may comprise: a first priming site (P1); a second priming site (P2); an insert; an internal adaptor (IA); and a barcode (BC). In some embodiments, a fragment library may include constructs having certain arrangements, such as: a P1 priming site, an insert, an internal adaptor (IA), a barcode (BC), and a P2 priming site. In some embodiments, the fragment library may be attached to a solid support, such as a bead.

Figure 11:
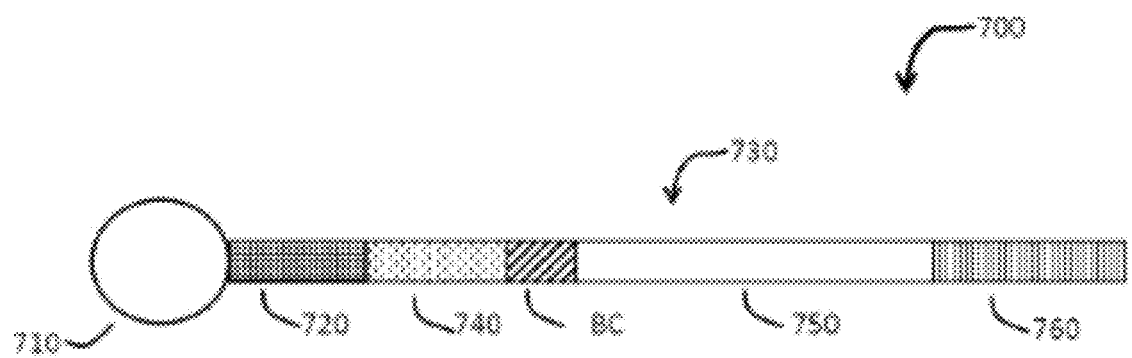
FIG. 11 illustrates an exemplary beaded template comprising a barcode sequence.

FIG. 11 illustrates an exemplary beaded template in accordance with an embodiment of the fragment library. It shows an exemplary nucleic acid attached to a solid support, such as a bead. A beaded template 700 includes a bead 710 having a linker 720, which is a sequence for attaching a template 730 to the solid support. The template 730 may include a first or P1 priming site 740, an insert 750, and a second or P2 priming site 760. The template 730 may be a synthetic template. The template 730 may be representative of a fragment library. The template 730 may comprise a nucleic acid barcode BC, which may be positioned between the P1 priming site 740 and the insert 750, for example. An internal adaptor may be placed between the P1 priming site 740 and the barcode BC, or between the barcode BC and the insert 750, or between the insert 750 and the P2 priming site 760.

Figure 12:
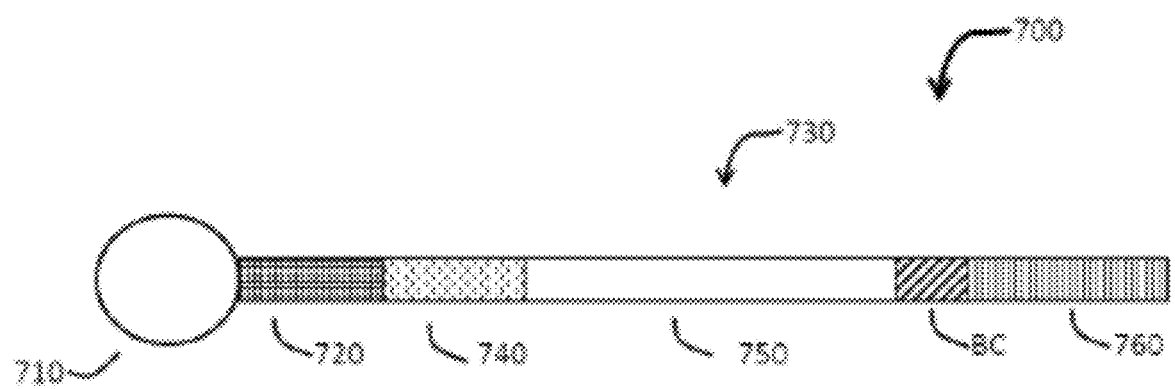
FIG. 12 illustrates another exemplary beaded template comprising a barcode sequence.

FIG. 12 illustrates another exemplary beaded template in accordance with an embodiment of the fragment library. The nucleic acid barcode BC may be positioned between the insert 750 and the P2 priming site 760. An internal adaptor may be placed between the P1 priming site 740 and the insert 750, or between the insert 750 and the barcode BC, or between the barcode BC and the P2 priming site 760.

In various embodiments, the length of the linker 720 and template 730 may vary. For example, the length of the linker 720 may range from 10 to 100 bases, for example, or from 15 to 45 bases, for example, and may be 18 bases (18b) in length, for example. The template 730, which comprises the P1 priming site 740, the insert 750, and the P2 priming site 760, may also vary in length. For example, the P1 priming site 740 and the P2 priming site 760 may each range from 10 to 100 bases, for example, or from 15 to 45 bases, for example, and may be 23 bases (23b) in length, for example. The insert 750 may range from 2 bases (2b) to 20,000 bases (20 kb), for example, and may be 60 bases (60b), for example. In an embodiment, the insert 750 may comprise more than 100 bases, such as, e.g., 1,000 or more bases. In various embodiments, the insert may be in the form of a concatenate, in which case, the insert 750 may comprise up to 100,000 bases (100 kb) or more.

In various embodiments, the position of barcode BC may be selected based on various considerations, such as the length of the insert, signal-to-noise ratio issues, and/or sequencing bias issues. For example, where signal-to-noise ratio may be an issue (e.g., the signal-to-noise ratio can decrease as additional ligation cycles are performed in sequencing-by-ligation, for example), the barcode BC may be positioned adjacent the P1 priming site 740 to mitigate against potential errors due to a diminished signal-to-noise ratio. Where the signal-to-noise ratio may not be a significant issue, the barcode BC may be placed adjacent to either the P1 priming site 740 or the P2 priming site 760. In some cases, template sequences may interact differently with a probe sequence used during the sequencing experiment. Placing the barcode BC before the insert 750 can affect the sequencing results for the insert 750. Positioning the barcode BC after the insert 750 can decrease sequencing errors due to bias. Generally, the position of the barcode can be affected by or affect sequencing, and the position that best achieves desired results based on the conditions of the sequencing process may be selected.

In various embodiments, sequencing and decoding of a nucleic acid barcode may be performed with a single forward direction sequence read (e.g., 5'-3' direction along the template), e.g., reading the barcode BC and the insert 750 in a single read. In an embodiment, the forward read may be parsed into the barcode portion and the insert portion algorithmically.

In addition to the fragment library and corresponding beaded templates described herein, additional libraries and/or beaded templates may also be implemented with the disclosed barcodes. For example, U.S. patent application Ser. No. 13/599,876, published Feb. 28, 2015 as U.S. Patent Pub. No. 2013/0053256, to Hubbell, entitled METHODS, SYSTEMS, AND KITS FOR SAMPLE IDENTIFICATION, which is incorporated herein by reference in its entirety, further discloses Mate Pair Libraries, Paired End Libraries, SAGE libraries, Yeast libraries, and ChIP-Seq libraries that may be implemented with various disclosed embodiments.

According to various embodiments, one or more features of any one or more of the above-discussed teachings and/or embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various embodiments, one or more features of any one or more of the above-discussed teachings and/or embodiments may be performed or implemented using appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and nonvolatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various embodiments, one or more features of any one or more of the above-discussed teachings and/or embodiments may be performed or implemented at least partly using a distributed, clustered, remote, or cloud computing resource.

According to various embodiments, one or more features of any one or more of the above-discussed teachings and/or embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various embodiments, one or more of the above-discussed embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various other embodiments may be derived by repeating, adding, or substituting any generically or specifically described features and/or components and/or substances and/or steps and/or operating conditions set forth in one or more of the above-described embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed embodiments may be considered to be a potential optional feature, component, aspect, step, or other characteristic of any other of the above-discussed embodiments so long as the objective of such any other of the above-discussed embodiments remains achievable, unless specifically stated otherwise.

Although various embodiments of the present teachings may advantageously be used with sequencing-by-synthesis approaches, as described herein and in Rothberg et al., U.S. Pat. Publ. No. 2009/0026082; Anderson et al., SENSORS AND ACTUATORS B CHEM., 129:79-86 (2008); Pourmand et al., PROC. NATL. ACAD. SCI., 103:6466-6470 (2006), which are all incorporated by reference herein in their entirety, for example, the present teachings may also be used with other approaches, such as variants of sequencing-by-synthesis including methods where the nucleotides or nucleoside triphosphate precursors are modified to be reversible terminators (sometimes referred to as cyclic reversible termination (CRT) methods) and methods where the nucleotides or nucleoside triphosphate precursors are unmodified (sometimes referred to as cyclic single base delivery (CSD) methods), for example, or more generally methods that comprise repeated steps of delivering (or extending in response to delivering) nucleotides (to the polymerase-primer-template complex) and collecting signals (or detecting the incorporation either directly or indirectly).

Although various embodiments of the present teachings may advantageously be used in connection with pH-based sequence detection, as described herein and in Rothberg et al., U.S. Pat. Appl. Publ. Nos. 2009/0127589 and 2009/0026082 and Rothberg et al., U.K. Pat. Appl. Publ. No. GB2461127, which are all incorporated by reference herein in their entirety, for example, the present teachings may also be used with other detection approaches, including the detection of pyrophosphate (PPi) released by the incorporation reaction (see, e.g., U.S. Pat. Nos. 6,210,891; 6,258,568; and 6,828,100); various fluorescence-based sequencing instrumentation (see, e.g., U.S. Pat. Nos. 7,211,390; 7,244,559; and 7,264,929); some sequencing-by-synthesis techniques that can detect labels associated with the nucleotides, such as mass tags, fluorescent, and/or chemiluminescent labels (in which case an inactivation step may be included in the workflow (e.g., by chemical cleavage or photobleaching) prior to the next cycle of synthesis and detection)); and more generally methods where an incorporation reaction generates or results in a product or constituent with a property capable of being monitored and used to detect the incorporation event, including, for example, changes in magnitude (e.g., heat) or concentration (e.g., pyrophosphate and/or hydrogen ions), and signal (e.g., fluorescence, chemiluminescence, light generation), in which cases the amount of the detected product or constituent may be monotonically related to the number of incorporation events, for example.

Although the present description described in detail certain embodiments, other embodiments are also possible and within the scope of the present invention. For example, those skilled in the art may appreciate from the present description that the present teachings may be implemented in a variety of forms, for example, using various sequencing instruments, and that the various embodiments may be implemented alone or in combination. Variations and modifications will be apparent to those skilled in the art from consideration of the specification and figures and practice of the teachings described in the specification and figures, and the claims.

Table 2 shows representative barcode sequences in accordance with various embodiments described herein.

| Seq. I.D. | Barcode Sequence | Group Designation |
|---|---|---|
| (SEQ. ID. NO. 20) | TTCCGGAGGATGCC | plate_XX |
| (SEQ. ID. NO. 21) | TTGAGGCCAAGTCC | plate_XX |
| (SEQ. ID. NO. 22) | GACCACCGGTTC | plate_XX |
| (SEQ. ID. NO. 23) | GTGGACCTCCGTTC | plate_XX |
| (SEQ. ID. NO. 24) | TGGACCACGAATTC | plate_XX |
| (SEQ. ID. NO. 25) | TTCTGGACATCCGC | plate_XX |
| (SEQ. ID. NO. 26) | TTAGGCCTCCATTC | plate_XX |
| (SEQ. ID. NO. 27) | GTTGAGGAACCACC | plate_XX |
| (SEQ. ID. NO. 28) | CCGGACAAGAATTC | plate_XX |
| (SEQ. ID. NO. 29) | CGGAGTTCCGGTTC | plate_XX |
| (SEQ. ID. NO. 30) | GTCCACCAACCACC | plate_XX |
| (SEQ. ID. NO. 31) | GTTCCAGCCATCTC | plate_XX |
| (SEQ. ID. NO. 32) | GTTAGCGGATTC | plate_XX |
| (SEQ. ID. NO. 33) | GCCACAACTTCC | plate_XX |
| (SEQ. ID. NO. 34) | GTTCCTTAGAAGAC | plate_XX |
| (SEQ. ID. NO. 35) | GCCAGCACCAATTC | plate_XX |
| (SEQ. ID. NO. 36) | GCTTGGAGCCGTTC | plate_01 |
| (SEQ. ID. NO. 37) | TCCAGGCACCTTCC | plate_01 |
| (SEQ. ID. NO. 38) | GTTCCTACGTTC | plate_01 |
| (SEQ. ID. NO. 39) | CCAGAACGGAATCC | plate_01 |
| (SEQ. ID. NO. 40) | GTCAGGACCAAC | plate_02 |
| (SEQ. ID. NO. 41) | CTTACCATCCTTCC | plate_02 |
| (SEQ. ID. NO. 42) | GCTGACACCACC | plate_02 |
| (SEQ. ID. NO. 43) | TCACCAACGGAC | plate_02 |
| (SEQ. ID. NO. 44) | CTGAGAATCCAACC | plate_02 |
| (SEQ. ID. NO. 45) | TTCCTACAATCTCC | plate_02 |
| (SEQ. ID. NO. 46) | GTCTTGACAAGAAC | plate_02 |
| (SEQ. ID. NO. 47) | GTTCTTAGAGAACC | plate_02 |
| (SEQ. ID. NO. 48) | GTCCAGGAGGTC | plate_02 |
| (SEQ. ID. NO. 49) | TCGGACCAATTGCC | plate_02 |

| Seq. I.D. | Barcode Sequence | Group Designation |
|---|---|---|
| (SEQ. ID. NO. 50) | CCTTACCAATAACC | plate_03 |
| (SEQ. ID. NO. 51) | TCGAGGCCATCGAC | plate_03 |
| (SEQ. ID. NO. 52) | TTCCTTACCTTATC | plate_03 |
| (SEQ. ID. NO. 53) | TTCTGAGCCGAC | plate_03 |
| (SEQ. ID. NO. 54) | GTCCTACCAATGAC | plate_03 |
| (SEQ. ID. NO. 55) | TAGCCAATTGAACC | plate_03 |
| (SEQ. ID. NO. 56) | GCCTTAGCAACACC | plate_03 |
| (SEQ. ID. NO. 57) | GTCCTGAGCAGAAC | plate_03 |
| (SEQ. ID. NO. 58) | GTCTACCTCGGC | plate_03 |
| (SEQ. ID. NO. 59) | GTCTGACCGGATCC | plate_03 |
| (SEQ. ID. NO. 60) | CCAGAATTCGGACC | plate_04 |
| (SEQ. ID. NO. 61) | TTCCGGAGTTCATC | plate_04 |
| (SEQ. ID. NO. 62) | CCTTAGATCCTTCC | plate_04 |
| (SEQ. ID. NO. 63) | GCCTTAGGATCGCC | plate_04 |
| (SEQ. ID. NO. 64) | GCCAGGATTGGTCC | plate_04 |
| (SEQ. ID. NO. 65) | GTCCGGAGATGAAC | plate_04 |
| (SEQ. ID. NO. 66) | GCCTTATTCCAACC | plate_04 |
| (SEQ. ID. NO. 67) | GTTCTAGGATTCAC | plate_04 |
| (SEQ. ID. NO. 68) | TCCTAGTCCGGTCC | plate_04 |
| (SEQ. ID. NO. 69) | GTCTTGGAGTTAAC | plate_04 |
| (SEQ. ID. NO. 70) | GTTCTATCGTTC | plate_05 |
| (SEQ. ID. NO. 71) | TTCGAGTGTTCC | plate_05 |
| (SEQ. ID. NO. 72) | TCTTGATTGGTC | plate_05 |
| (SEQ. ID. NO. 73) | GCTTACTCCGGTCC | plate_05 |
| (SEQ. ID. NO. 74) | GATTCGGATTCC | plate_05 |
| (SEQ. ID. NO. 75) | GTTCCTGAGTTCTC | plate_05 |
| (SEQ. ID. NO. 76) | GTCGGACCATGAAC | plate_05 |
| (SEQ. ID. NO. 77) | CAGATCCGTTCC | plate_05 |
| (SEQ. ID. NO. 78) | GTTCTGACGTCC | plate_05 |
| (SEQ. ID. NO. 79) | TCCGAGGATGAATC | plate_05 |

We claim:

1. A method of manufacturing polynucleotide templates for use in nucleic acid sequencing, the method comprising:
generating a set of flowspace codewords, the flowspace codewords comprising strings of characters, each flowspace codeword comprising a distinct string of characters;
determining a location for at least one padding character within the flowspace codewords;
inserting the at least one padding character into the flowspace codewords at the determined location;
selecting, after the inserting, a subset of flowspace codewords from the set, wherein each flowspace codeword of the subset satisfies a predetermined minimum distance and is configured to be expressed in flowspace according to a predetermined flow order; and
manufacturing polynucleotide templates, each polynucleotide template comprising:
a respective barcode sequence corresponding to a flowspace codeword from the subset, and
a series of key bases appended to the respective barcode sequence, wherein:
for a first group of the subset, the series of key bases appended to the respective barcode sequences terminates with a repeated base,
for a second group of the subset, the series of key bases appended to the respective barcode sequences terminates with a non-repeating base,
the subset of flowspace codewords collectively defines an error tolerant code that provides a minimum distance between flowspace codewords of the subset, and
a variance in the key bases appended to the flowspace codewords of the subset increases the minimum distance between the flowspace codewords of the subset.

2. The method of claim 1, further comprising after the inserting, filtering out at least one flowspace codeword from the subset that is not configured to be expressed in flowspace according to the predetermined flow order.

3. The method of claim 1, wherein determining a location for the padding character within the set of flowspace codewords further comprises:
iterating over a plurality of locations for the padding character within the set of flowspace codewords;

for each iteration, calculating a number of flowspace codewords that are configured to be expressed in flowspace according to the predetermined flow order; and selecting the location of the plurality of locations with the highest calculated number of flowspace codewords that are configured to be expressed in flowspace according to the predetermined flow order.

4. The method of claim 3, wherein the subset of flowspace codewords of the error tolerant code are synchronized in flowspace after insertion of the at least one padding character.

5. The method of claim 1, wherein the flowspace codewords of the set comprise a preliminary distance between the flowspace codewords such that the minimum distance between the flowspace codewords of the subset is greater than the minimum distance between the flowspace codewords of the set.

6. The method of claim 5, wherein the preliminary distance between the flowspace codewords of the set is maintained after insertion of the padding character.

7. The method of claim 6, further comprising:

grouping the flowspace codewords of the subset into a plurality of groups such that an inner-group minimum distance between flowspace codewords within a group comprises a first value and an outer-group minimum distance for flowspace codewords between different groups comprises a second value, the first value being greater than the second value.

8. The method of claim 1, wherein the first group comprises half of a total number of the barcode sequences of the subset.

9. The method of claim 1, further comprising attaching the polynucleotide templates to one or more solid phase supports.

10. The method of claim 1, wherein each polynucleotide template comprises an insert sequence.

11. The method of claim 10, wherein the insert sequence is located adjacent to the respective barcode sequences of the polynucleotide templates.

12. The method of claim 10, wherein each polynucleotide template comprises a first priming sequence and a second priming sequence, and the respective barcode sequence is located between the first and second priming sequences.

13. The method of claim 12, wherein each respective barcode sequence is located between the insert sequence and one of the first priming sequence or the second priming sequence.

14. The method of claim 1, wherein each polynucleotide template comprises a linker sequence enabling attachment of the polynucleotide template to a solid support.

15. The method of claim 1, further comprising purifying the polynucleotide templates using High Performance Liquid Chromatography (HPLC), a desalting technique, or both.

16. The method of claim 1, further comprising assembling the manufactured polynucleotide templates into a library of polynucleotide templates for use in nucleic acid sequencing.

* * * * *